United States Patent [19]

Tsuchiya

[11] Patent Number: 5,517,987
[45] Date of Patent: May 21, 1996

[54] METHOD FOR MEASURING INTERNAL INFORMATION IN SCATTERING MEDIUM AND APPARATUS FOR THE SAME

[75] Inventor: Yutaka Tsuchiya, Hamamatsu, Japan

[73] Assignee: Hamamatsu Photonics K.K., Hamamatsu, Japan

[21] Appl. No.: 252,227

[22] Filed: Jun. 1, 1994

[30] Foreign Application Priority Data

Jun. 2, 1993 [JP] Japan ................................. 5-132211
Feb. 18, 1994 [JP] Japan ................................. 6-021400

[51] Int. Cl.$^6$ ........................................ A61B 5/00
[52] U.S. Cl. .......................................... 128/633
[58] Field of Search ...................... 128/633, 664, 128/665

[56] References Cited

U.S. PATENT DOCUMENTS

| | | | |
|---|---|---|---|
| 5,057,695 | 10/1991 | Hirao et al. | 128/633 |
| 5,277,181 | 1/1994 | Mendelson et al. | 128/633 |
| 5,285,783 | 2/1994 | Secker | 128/633 |
| 5,297,548 | 3/1994 | Pologe | 128/633 |
| 5,333,610 | 8/1994 | Hirao | 128/633 |
| 5,372,135 | 12/1994 | Mendelson et al. | 128/633 |

FOREIGN PATENT DOCUMENTS

| | | | |
|---|---|---|---|
| 64-88340 | 4/1989 | Japan. | |
| 1174940 | 7/1989 | Japan. | |
| 4110751 | 4/1992 | Japan. | |
| 2228314 | 8/1990 | United Kingdom. | |
| 8912223 | 12/1989 | WIPO. | |
| 9004941 | 5/1990 | WIPO. | |
| 9201216 | 1/1992 | WIPO. | |
| 9221283 | 12/1992 | WIPO | 128/633 |

OTHER PUBLICATIONS

Graaff et al, "Optical Properties of Human Dermis In Vitro and In Vivo", Applied Optics, vol. 32, No. 4, Feb. 1, 1993, pp. 435–447.

Farrell et al, "A Diffusion Theory Model of Spatially Resolved, Steady–State Diffuse Reflectance for the Noninvasive Determination of Tissue Optical Properties In Vivo" Med. Physics, vol. 19, No. 4, Jul. 1992, pp. 879–888.

Farrell et al, "The Use of a Neural Network to Determine Tissue Optical Properties From Spatially Resolved Diffuse Reflectance Measurements", Phys. Med. Biol., vol. 37, No. 12, 1192, pp. 2281–2286.

Wilson et al, "Optical Reflectance and Transmittance of Tissues: Principles and Applications", IEEE Journal of Quantum Electronics, vol. 26, No. 12, Dec. 1990, pp. 2186–2199.

I. Oda et al, "Non–Invasive Hemoglobin Oxygenation Monitor and Computed Tomography By NIR Spectrophotometry", pp. 284–293, SPIE, vol. 1431, 1991.

(List continued on next page.)

*Primary Examiner*—Angela D. Sykes
*Assistant Examiner*—Eric F. Winakur
*Attorney, Agent, or Firm*—Cushman Darby & Cushman

[57] ABSTRACT

A method of measuring internal information in a scattering medium, and an apparatus for the same of the present invention measure internal information in the scattering medium by measuring light diffused during propagation in the scattering medium while receiving the influence of the scattering and absorption, and performing arithmetic processing to the measured values. At this time, the three or more kinds of the detected signals (measured values) measured at three or more different kinds of distances between the light incident position and the photodetection point are processed by utilizing dependencies of the behavior of light diffused during propagation in the scattering medium and the resulting signal, that is, a photodetection signal on characteristics such as a scattering constituent, or an absorption constituent in the scattering medium and the concentration. The measured internal information is the absolute value of a scattering coefficient or a transport scattering coefficient of the scattering medium, and the information associated with a specified scattering constituent or a specified absorption constituent can be measured by processing the measured internal information.

23 Claims, 15 Drawing Sheets

STRUCTURE OF APPARATUS OF THE FIRST EMBODIMENT

OTHER PUBLICATIONS

M. S. Patterson et al, "Time–Resolved Reflectance and Transmittance for the Non–Invasive Measurement of Tissue Optical Properties", pp. 2331–2336, Applied Optics, vol. 28, No. 12, Jun. 15, 1989.

M. S. Patterson et al. "Applications of Time–Resolved Light Scattering Measurements to Photodynamic Therapy Dosimetry", pp. 62–75, SPIE, vol. 1203, 1990.

E. M. Sevick et al, "Time–Dependent Photon Migration Imaging", pp. 273–283, SPIE, vol. 1599, 1991.

BEHAVIOR OF LIGHT IN SCATTERING MEDIUM

RELATION BETWEEN DETECTED QUANTITY OF
LIGHT I[$\rho$] AND DETECTION DISTANCE $\rho$

PRINCIPLE OF THE PRESENT INVENTION

NEAR-INFRARED ABSORPTION SPECTRA
OF Hb(0.37mM) AND Mb(0.15mM)

ABSOLUTE SPECTRUM
SOLID LINE : OXYGENATED
DOTTED LINE : DEOXYGENATED

ABSORPTION SPECTRA OF VARIOUS
BIOLOGICAL MATERIALS

PRINCIPLE OF MEASUREMENT FOR SLAB-LIKE SPECIMEN

STRUCTURE OF APPARATUS OF THE FIRST EMBODIMENT

SWITCHING OF LIGHT HAVING DIFFERENT WAVELENGTHS

MIXING OF LIGHTS HAVING DIFFERENT WAVELENGTH

DETECTION OF LIGHTS HAVING DIFFERENT WAVELENGTHS

CONDENSER LENS

OPTICAL FIBER

PINHOLE

LIGHT INCIDENCE FROM THE INSIDE OF SCATTERING MEDIUM

METHAD OF CAUSING LIGHT TO BE INCIDENT ON SCATTERING MEDIUM

DIRECT DETECTION

OPTICAL FIBER

LENS COUPLING

NARROW-BAND AMPLIFIER

LOCK-IN AMPLIFIER

STRUCTURE OF MAIN PART OF APPARATUS OF THE THIRD EMBODIMENT

DETAILED STRUCTURE OF LIGHT INCIDENT POSITION AND PHOTODETECTION POINT OF MODIFICATION OF APPARATUS OF THE THIRD EMBODIMENT

METHOD FOR MEASURING INTERNAL INFORMATION IN SCATTERING MEDIUM AND APPARATUS FOR THE SAME

BACKGROUND OF THE INVENTION

1. Field of the Invention

The present invention relates to non-invasive measurement of internal information in a scattering medium by causing pulsed light, square wave light, or continuous light to be incident on a scattering medium such as a living body, and detecting light propagating in the scattering medium. More particularly present invention relates to a method for measuring internal information in a scattering medium and an apparatus for the same, which are capable of measuring an absolute value of an absorption coefficient and a transport scattering coefficient of the scattering medium, the concentration of a specific absorptive constituent in the scattering medium, its time change, and its spatial distribution.

2. Related Background Art

Demands for precise measurement of an absorption coefficient or a transport scattering coefficient in a scattering medium such as a living body or the precise measurement of the concentration of a specific absorptive constituent are very strong, and there have been several reports and attempts for such measurement. The main prior arts are listed as references 1.–5. at the end of this section.

In general, since light is scattered and/or absorbed at random in a scattering medium, light does not propagate in a straight line. For a scattering medium in which the absorption is zero, the total quantity of light never decreases, but since light is scattered by scattering constituents at random, light propagates in a zigzag manner. In this case, the distance that light can propagate without any effect of scattering is called a mean free path or a mean diffusion length, which is the inverse of a transport scattering coefficient $\mu_s'$. In the case of the living body specimen, the mean free path is about 2 mm. Such is disclosed in Wilson et al., Optical Reflectance and Transmittance of Tissues, Principle and Application, IEEE J. Quantum Electron, Vol. 26, No. 12, pp. 2186–2199. In addition, the scattering medium comprises absorptive constituents other than the scattering constituents, so that the absorption occurs in accordance with a distance that light propagates while scattering, and the quantity of light is exponentially attenuated in accordance with the distance.

As the prior art in the field of precise measurement of an absorption coefficient or a transport scattering coefficient of a scattering medium, one document teaches measuring the quantity of transmitted light or reflected light corresponding to continuous light or pulsed light incidence, and one document teaches measuring the transmitted light or reflected light corresponding to pulsed light incidence and to analyze its waveform. The former utilizes a measurement of the absorbance in which the Lambert-Beer Law is a basic principle, and there a further document utilizes a principle of dual-wavelength spectroscopy. Here, Lambert-Beer law is that the absorbance of the specimen is proportional to the product of the molar absorption coefficient, molar concentration, and a specimen thickness, and that a difference of the absorbances is proportional to the concentration difference where a thickness of the specimen is constant.

However, in the case of the absorbance optical density measurement in the scattering medium, a mean optical pathlength of light diffused during propagation between a light incident position and a photodetection point is varied depending on the absorption coefficient $\mu_a$ of the scattering medium. Therefore, in the absorbance measurement corresponding to the scattering medium in which the optical pathlength is constant, an absorption coefficient dependency of the mean optical pathlength is a big problem, which hinders the precise measurement of an absorption coefficient or the concentration of an absorptive constituent, or if the measurement is performed, due to large errors in measurement, it cannot practically be used. For example, according to "Japanese Patent Application No. Sho 62-248590", "Japanese Patent Application No. Sho 62-336197", and "Japanese Patent Application No. Hei 2-231378", since a basic principle is to measure an optical coefficient in which an optical pathlength is assumed to be constant, errors in measurement caused by a change of the above-described optical pathlength cannot be avoided.

There is another method utilizing a mean optical pathlength which is measured by another method in the case of an absorbance measurement, bun hence a mean optical pathlength is varied depending on the absorption coefficient, errors caused by approximating the average optical pathlength to be a constant value cannot be avoided. Further, there are a method of measuring an absorbance difference using pulsed light, a method further utilizing a principle of dual-wavelength spectroscopy, and a method of measuring an absorbance optical density using light having three or more kinds of wavelengths, but in either case, since a method of measuring an absorbance in which an optical pathlength in a scattering medium is assumed to be constant is applied, errors caused by the change of the optical pathlength occur in the all cases, so that the sufficient precise measurement can not be performed.

In the prior art not based on an absorbance measurement, a method, in which transmitted light or reflected light is measured by time-resolved measurement using pulsed light or modulated light to analyze waveform, has disadvantages that owing to the time-resolved measurement, the measurement method and the apparatus are very complicated and the apparatus is expensive, as compared with a measurement method and an apparatus according to the present invention in which quantity of light, that is, time integration of an optical signal is measured. There are several attempts for measuring internal absorption information by measuring reflected light or transmitted light upon the incidence of pulsed light to the medium by the time-resolved measurement and analyzing its waveform. This is suggested in Patterson et al., "Time Resolved Reflectance and Transmittance, for the Non-Invasive Measurement of Tissue Optical Properties, Applied Optics, Vol. 28, No. 12, pp. 2331–2336 (1989); Patterson et al., Applications of Time-Resolved Light Scattering Measurements to Photodynamic Therapy Dosimetry, Proc. SPIE, Vol.1203, pp. 62–75 (1990); and Sevick et al., Time-Dependent Photon Migration Imaging, Proc. SPIE, Vol. 1599, pp. 273–283 (1991). A measured optical signal has a long decay tail by the influence of scattering and absorption constituents. Patterson et al. assumes a model of uniform scattering medium to analytically obtain the light signal output. See Patterson et al. (1989). A wave representing a time change in intensity of the optical output signal given by the formula defined by Patterson et al. matches a waveform obtained by an experiment using a uniform scattering medium. According to Patterson et al. and the results of the experiment by the inventor of the present application, the absorption coefficient of absorptive constituents in the scattering medium is given by a slope of a waveform (differential coefficient) obtained when the optical signal is sufficiently attenuated, i.e., when a sufficiently long period has elapsed. However, because the optical signal at a location where an absorption coefficient is obtained required to be sufficiently attenuated means that the signal is very feeble, a signal to noise ratio (S/N) of the signal to measured is decreased, and consequently errors in measurement are increased. Therefore, such a system and method are hard to use in practical application. There are several kinds of attempts other than the above, but none of them gives sufficient measurement precision.

A method which utilizes the above-stated dual-wavelength spectroscopy measurement to a scattering medium has the following problems. In the absorbance measurement of a scattering medium, an extinction coefficient is a sum of a transport scattering coefficient and an absorption coefficient by definition. Since these parameters are treated at the same level, the absorption influence, e.g., an absorption coefficient, cannot be measured while scattering and absorption influences cannot be separated. In general, this can be solved by using a principle of dual-wavelength spectroscopy measurement, an absorption coefficient is measured by using two or more suitable kinds of lights having different absorption coefficients resulting in different absorption constituents, and assuming that a scattering coefficient and a transport scattering coefficient of the two or more kinds of lights are the same, or if they are different, assuming that the difference is very small, the scattering influence is eliminated from an absorbance optical density difference corresponding to two or more kinds of light to obtain the concentration of an absorption constituent or an absorption coefficient. This method has a disadvantage of the occurrence of errors caused by the assumption that scattering coefficients or transport scattering coefficients corresponding to different wavelengths are equal.

REFERENCES

1) B. C. Wilson and S. L. Jacques: Optical Reflectance and Transmittance of Tissues: Principle and Application, IEEE J. Quantum Electron., Vol. 26, No. 12, pp. 2186–2199 (1990)

2) I. Oda, Y. Ito, H. Eda, T. Tamura, M. Takada, R. Abumi, K. Nagai, H. Nakagawa, and M. Tamura: Non-invasive hemoglobin oxygenation monitor and computed tomography by NIR spectrophotometry, Proc. SPIE, Vol. 1431, pp. 284–293 (1991)

3) M. S. Patterson, B. Chance, and B. C. Wilson: Time resolved reflectance and transmittance for the non-invasive measurement of tissue optical properties, Applied Optics, Vol. 28, No. 12, pp. 2331–2336 (1989)

4) M. S. Patterson, J. D. Moulton, B. C. Wilson, and B. Chance: Application of time-resolved light scattering measurements to photodynamic therapy dosimetry, Proc. SPIE, Vol. 1203, pp. 62–75 (1990)

5) E. M. Sevick, N. G. Wang, and B. Chance: Time-dependent photon imaging, Proc. SPIE, Vol. 1599, pp. 273–283 (1991)

SUMMARY OF THE INVENTION

Measurement methods and measurement apparatus in the above-described field which have been developed and reported have not yet satisfied the desired measurement precision. The inventor of the present application theoretically and experimentally analyzed and examined the behavior of light in a scattering medium which is a basis of the measurement in the above-described field, and found that the conventional analysis methods are insufficient to describe the complicated behavior of light in the scattering medium, and that most of the approximations used in the process of deriving a principle of the conventional measurement methods and the conventional measurement apparatus do not hold the in the actual object to be measured and the measurement field, which results in large errors included in the measured value. It is an object of the present invention to provide a new measurement method and a measurement apparatus which enhance the measurement precision while the errors are drastically decreased based on the above analyses, examinations, and experiments.

A method of measuring internal information in a scattering medium and an apparatus for measuring the internal information such as an absolute value of an absorption coefficient or a transport scattering coefficient in the scattering medium utilizing new knowledge in which a change of optical pathlength is taken into consideration, that is, a plurality of simultaneous relations between photodetection signals (measured values) when light having a predetermined wavelength is diffused while propagation in the scattering medium and reaches at predetermined photodetection points and a plurality of known parameters is disclosed herein. Further, information related to absorption such as the concentration of a specified absorptive constituent is measured by performing the above measurement using light having a plurality of wavelengths.

A method of measuring internal information in a scattering medium of the present invention comprises (a) causing light having a predetermined wavelength to be incident on the scattering medium, (b) detecting light having the predetermined wavelength diffused during propagation in the scattering medium at detection points corresponding to three or more kinds of points where the distance between a light incidence position and a photodetection point is different to obtain the three or more kinds of the detected signals, and (c) extracting internal information in the scattering medium by performing arithmetic processing to the detected signals based on three or more kinds of simultaneous relations between a scattering characteristic and an absorption characteristic on a diffusion-propagation path in said scattering medium when the light having the predetermined wavelength is diffused during propagation and reaches at said detection points, and the detected signals.

Here, the light having the predetermined wavelength may be light having two or more kinds of wavelengths, each having a different absorption coefficient to a specified absorptive constituent of the scattering medium, and the arithmetic processing may comprise a process of extracting primary internal information in the scattering medium obtained by the measurement with one kind of the predetermined wavelength, and a process of extracting secondary internal information in the specified constituent of the scattering medium, utilizing the primary internal information corresponding to light having the two or more kinds of wavelengths.

An apparatus for measuring internal information in a scattering medium of the present invention comprises (a) light-emitting means for emitting light having a predetermined wavelength, (b) light-incident means for causing the light having the predetermined wavelength to be incident on the scattering medium, (c) photodetecting means for detecting light having the predetermined wavelength, diffused during propagation in the scattering medium at detection points corresponding to three or more kinds of points where the distance between a light incidence position and a photodetection point is different, and obtaining three or more kinds of the detected signals, and (d) arithmetic processing means for extracting internal information in the scattering medium by performing arithmetic processing to the detected signals, based on three or more kinds of simultaneous relations among a scattering characteristic and an absorption characteristic on a diffusion-propagation path in the scattering medium when the light having the predetermined wavelength is diffused during propagation and reaches at the detection points, and the detected signals.

Here, the light having the predetermined wavelength may be light having two or more kinds of wavelengths, each having a different absorption coefficient to a specified absorption constituent of the scattering medium, and the arithmetic processing means may execute a process of extracting primary internal information in the scattering medium obtained by the measurement with one kind of said predetermined wavelength, and a process of extracting secondary internal information in the specified constituent of the scattering medium, utilizing the primary internal information corresponding to light having the two or more kinds of wavelengths.

A method of measuring internal information in a scattering medium, and an apparatus for the same of the present invention measure internal information in the scattering medium by measuring light diffused during propagation in the scattering medium while receiving the influence of the scattering and absorption, and performing arithmetic processing to the measured values. At this time, the three or more kinds of the detected signals (measured values) measured at three or more different kinds of distances between the light incident position and the photodetection point are processed by utilizing a characteristic that the behavior of light diffused during propagation in the scattering medium and the resulting signal, i.e., a photodetection signal depends on characteristics and the concentration of a scattering constituent, or an absorption constituent in the scattering medium. The measured internal information is the absolute value of a scattering coefficient or a transport scattering coefficient of the scattering medium, and the information associated with a specified scattering constituent or a specified absorption constituent can be measured by processing the measured internal information. If the measurement is performed at a plurality of places on an object to be measured, the spatial distribution of the internal information can be measured, and if the measurement is performed at the same position and at different time, the time-change in the internal information can be measured.

In particular, in the method and apparatus of the present invention, light having a predetermined wavelength is caused to be incident on a scattering medium and light diffused during propagation in the scattering medium is detected at three or more kinds of distances between a light incident position and a photodetection point to obtain the three or more kinds of the detected signals (measured values). Next, the three or more kinds of detected signals (measured values) and the known parameters are processed to measure the internal information in the scattering medium based on the three or more simultaneous relations of scattering and absorption when the light having the predetermined wavelength reaches at the photodetection points, and the detected signals (measured values). The relation among the detected signals (measured values), the parameters, and the internal information in the scattering medium is disclosed in the present application for the first time.

When the above measurement is performed using light having a plurality of different wavelengths, selecting the predetermined wavelength to have the different absorption coefficients to the specified absorptive constituents in the scattering medium, the specified absorptive constituents in the scattering medium can be measured accurately. In the measurement of the present invention, since transport scattering coefficients and absorption coefficients at a plurality of wavelengths are measured at high precision, even in the case of specimens or wavelengths in which the scattering coefficient is different at two wavelengths, the absorption coefficient of the scattering medium can be measured at high precision. The dual-wavelength spectroscopy measurement is utilized in the precise measurement, e.g., the concentration of the specified material, the degree of oxygen saturation of hemoglobin and their spatial distribution and their time change.

Therefore, a problem of errors in measurement caused by the change of optical pathlength and a problem of the scattering coefficient difference between two wavelengths in the dual-wavelength spectroscopy measurement are solved, and the measurement precision is drastically improved. Further, since the present invention is not the time-resolved measurement method, but is a method of measuring the quantity of light, that is, the time integration value of a photodetection signal, the structure of the apparatus is very simple and as the utilization factor of light is improved, the measurement time becomes short, and the signal to noise ration (S/N ratio) is improved. Accordingly, the measurement or the monitoring of the concentration of oxygen in a brain of a human who is being operated on or exercising is made possible by the present invention.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

DETAILED DESCRIPTION OF THE PREFERRED EMBODIMENTS

Figure 1:
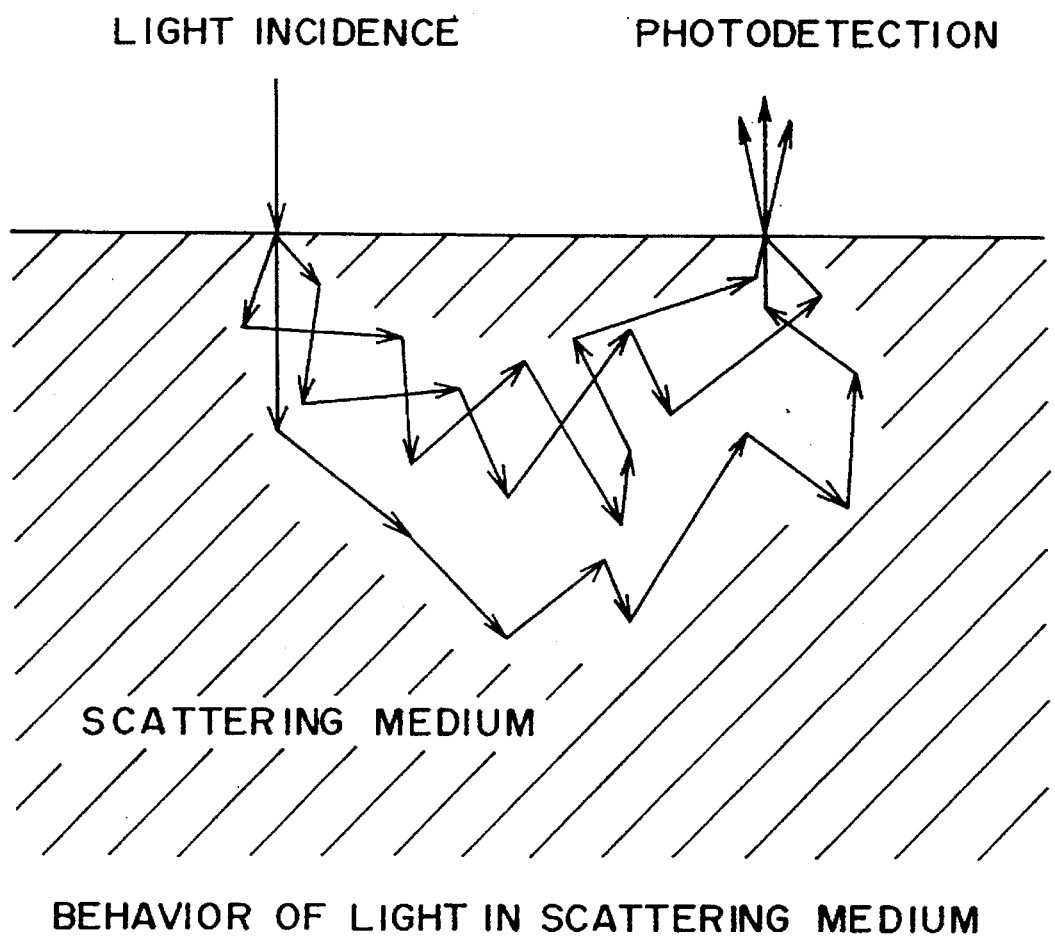
FIG. 1 is a view showing behavior of light in a scattering medium.

The embodiments of the present invention will be described in detail with reference to the accompanying drawings. The same parts are represented by the same reference numerals, and repetitive description thereof is omitted.

(1) Method of Measuring Internal Information of Scattering Medium (1.1) Principle of Internal Information Measurement of Scattering medium Light is scattered, absorbed and diffused during propagation in a scattering medium such as a living body and some light components emerge on a surface of the scattering medium. That is, light is scattered and absorbed in the scattering medium, but also can be transmitted therethrough. For example, FIG. 1 is a view showing behavior of light in the scattering medium and showing a state in which light is incident on one point of the scattering medium to detect diffusing light (reflected light) at other point. Light incident on the scattering medium is scattered at random and spreads all over the scattering medium, but in FIG. 1, only a track of photons detected by a photodetector is shown. In other words, FIG. 1 shows a track of photons which are utilized in practical measurement.

Figure 2:
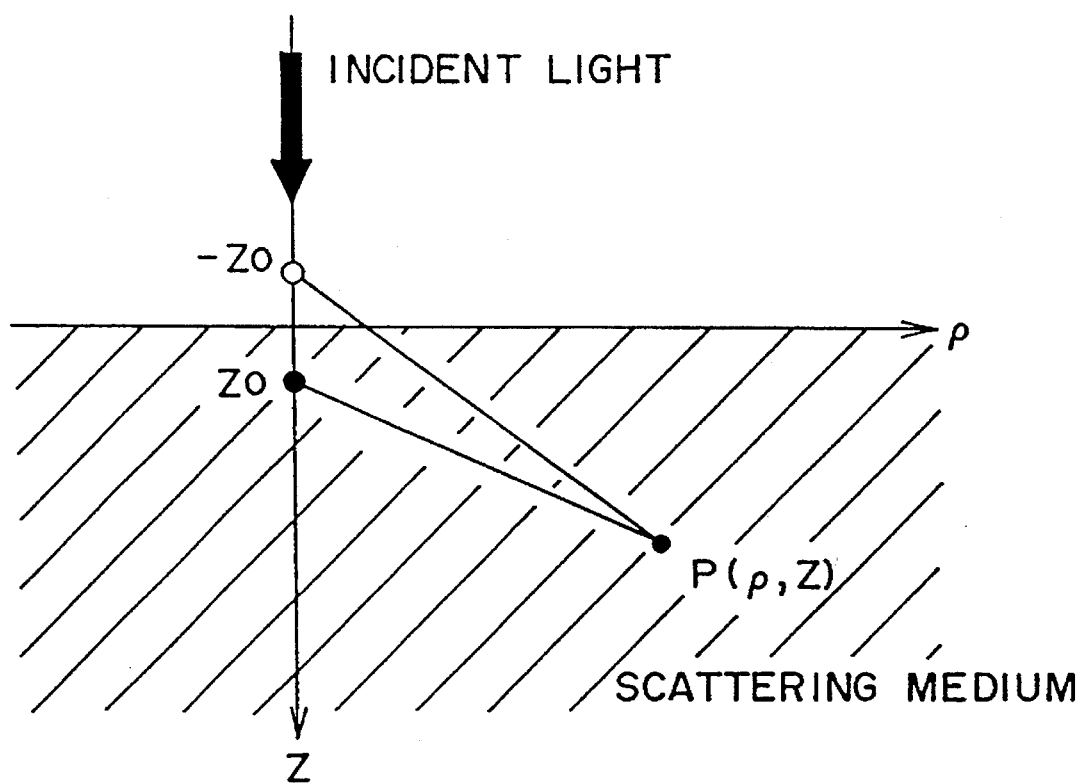
FIG. 2 is a view showing a way of obtaining quantity of detected light in an scattering medium.

It is known that the behavior of light in the scattering medium is precisely described and analyzed in accordance with a photon diffusion theory. According to the photon diffusion theory, a light pulse incident on the scattering medium has a pulse width that spreads as the light pulse is scattered, absorbed, and diffused during propagation in the scattering medium. FIG. 2 shows installation of a virtual light source to obtain quantity of light in the scattering medium. As shown in FIG. 2, when light is incident on a point ($\rho=0$, $z=0$) of a scattering medium surface, light to be detected at a point P ($\rho$, $z$), i.e., an optical signal is derived from a photon diffusion equation. In this case, since the photon diffusion is not present on the surface of the scattering medium and outside thereof, a boundary condition is required to be set to satisfy this requirement. Patterson et al. develop a method which satisfies the boundary condition by assuming a point light source of negative polarity and report that the theoretical values obtained from this method and the experimental values are well matched. In FIG. 2, the point light source of negative polarity is set at a o mark ($\rho=0$, $z=-z_0$).

On the other hand, the behavior of each photon diffused during propagation in the scattering medium can be analyzed, experimented, and examined in accordance with Monte Carlo calculation with the use of a computer. In addition, the experiment can be conducted with a physical model of a scattering medium or a living body specimen.

From the recent knowledge, the results derived from the photon diffusion theory, the results of Monte Carlo calculation, and the results of experiment with a sample are well matched. Therefore, it can be considered that the behavior of light in the scattering medium is sufficiently described by the photon diffusion equation. The various analyses, experiments, and examinations conducted by the present inventor and the recent accurate analyses and experiments of the behavior of light in the scattering medium confirm that the behavior of light in the scattering medium can precisely be described by the photon diffusion equation.

The photon diffusion equation which describes the behavior of light in the scattering medium as described above is, for example, expressed by a following equation using a photon fluence rate $\Phi$.

$$(1/c)(\partial\Phi(r,t)/\partial t) - D\nabla^2\Phi(r,t) + \mu_a\Phi(r,t) = S(r,t) \quad (1,1)$$

where $\Phi$: the photon fluence rate at position r, at time t [photon/mm$^2$·sec] (r is vector)

D: the diffusion coefficient [mm]

$\mu_a$: the absorption coefficient [mm$^{-1}$]

c: the speed [mm/sec] of light in a scattering medium (given by a refractive index)

S(r,t): light source [photon/mm$^3$·sec].

Since an impulsed light source can be expressed by a delta function, a light impulse incident on an origin (r=0) at t=0 can be expressed by the following equation.

$$S(r,t) = \delta(r,t) = \delta(0,0) = \delta(0)\cdot\delta(0) \quad (1.2)$$

Consequently, the photon diffusion equation corresponding to impulsed light incidence is as follows:

$$(1/c)(\partial\Phi(r,t)/\partial t) - D\nabla^2\Phi(r,t) + \mu_a\Phi(r,t) = \delta(0,0) \quad (1.3)$$

where $\delta(0,0)$ is a light impulsed incident on an origin (r=0) at t=0.

The various optical constants on a scattering medium are, for $\mu_s$: the scattering coefficient [mm$^{-1}$]

$\mu_s'$: the transport scattering coefficient [mm$^{-1}$]

$\mu_{tr}$: the transport attenuation coefficient [mm$^{-1}$]

$\mu_{eff}$: the effective attenuation coefficient [mm$^{-1}$]

g: the mean cosine $\theta$ of the scattering angle $\theta$, $$D = [3(\mu_a + \mu_s')]^{-1} = (3\mu_{tr})^{-1} \quad (1.4a)$$
$$\mu_s' = (1-g)\mu_s \quad (1.4b)$$
$$\mu_{tr} = \mu_a + \mu_s' = \mu_a + (1-g)\mu_s \quad (1.4c)$$
$$\mu_{eff} = [3\mu_a(\mu_a + \mu_s')]^{1/2}$$
$$= \{3\mu_a[\mu_a + (1-g)\mu_s]\}^{1/2}. \quad (1.4d)$$

In the case that a spot-like light pulse is incident on a semi-infinite scattering medium, a boundary condition is satisfied by providing a point light source of negative polarity at a location ($\rho=0$, $z=-z_0$) in accordance with Patterson et al. In general, $z_0$ is about $1/\mu_s'$, but strictly speaking, it varies depending on a light incidence method or characteristics of scattering constituents in a scattering medium. This is confirmed by the inventors of the present application with use of Monte Carlo calculation.

The photon diffusion equation (1.3) is solved under the above boundary condition, and an optical signal R($\rho$, 0, t)[photon/mm$^2$·sec] at an arbitrary location ($\rho$, 0) of the surface of the scattering medium is derived.

$$R(\rho,0,t) = (4\pi D)^{-3/2} z_0 t^{-5/2} \times \exp[-(z_0^2 + \rho^2)/(4cDt)] \times \exp(-c\mu_a t) \quad (1.5)$$

Since the detected quantity of light I[$\rho$] is a result of the time integration of R($\rho$, 0, t), it is expressed by $$I[\rho] = \int_0^\infty R(\rho, 0, t) dt \quad (1.6)$$

and this equation can be solved with use of integral formulas to obtain $$I[\rho] = z_0[\mu_{eff}(z_o^2 + \rho^2)^{1/2} + 1]/[2\pi (z_o^2 + \rho^2)^{3/2}] \times \exp[-\mu_{eff}(z_o^2 + \rho^2)^{1/2}] \quad (1.7)$$

Taking the natural logarithm of $I[\rho]$, $$\ln I[\rho] = \ln[z_0/(2\pi)] - (3/2)\ln(z_o^2 + \rho^2) + \quad (1.8)$$
$$\ln[\mu_{eff}(z_o^2 + \rho^2)^{1/2} + 1] - \mu_{eff}(z_o^2 + \rho^2)^{1/2}$$

Figure 3:
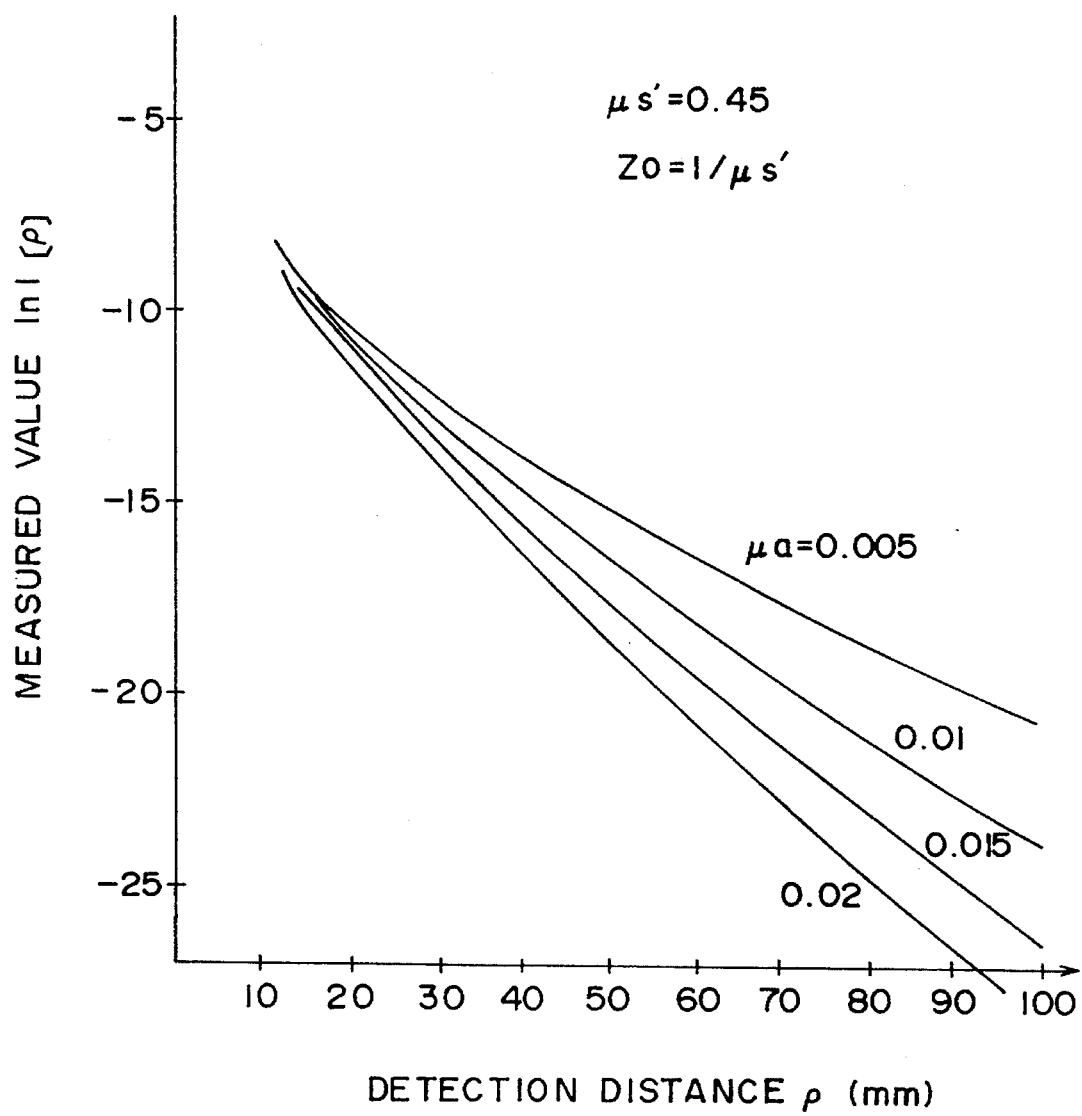
FIG. 3 is a graph showing relations between quantity of detected light I[ρ] and detection distance ρ.

Therefore, when $z_0$ is a known value, a measurement value $I[\rho]$ and a known value $\rho$ are substituted into equation (1.7) or (1.8) to derive Pelf in a scattering medium. FIG. 3 shows a relation between the measurement value $I[\rho]$ and a detection distance $\rho$. Here, $\mu_s'=0.45$ and $z_0=1/0.45$, and $\mu_a$ is shown as a parameter.

However, $z_0$ in the above-stated equations (1.7) and (1.8) is actually $z_0 \neq \mu_s'$. This can easily be understood with the next example. In the general measurement system, light is incident on a scattering medium from air, and light diffused during propagation in the scattering medium is detected in air. In this case, the above-described boundary condition, i.e., $z_0$, is a value which depends on the refractive index difference between the air and the scattering medium. According to the accurate analyses and Monte Carlo calculation by the inventor of the present invention, for $z_0=a/(\mu_a+\mu_s')$, it is confirmed that in the general measurement state, the value of a is within the range of $0.3<a<3$.

Further, when light is incident on the scattering medium or when light emerges from the scattering medium, if there is some light attenuation, for example, absorption by a surface colored layer, the optical signal R expressed by equation (1.5) and the detected quantity of light expressed by equation (1.7) or equation (1.8) are decreased in proportion to the attenuation. In general, the emerged light is detected by a photodetector. Therefore, the detecting signal (measured value) is a value related to the quantum efficiency of the photodetector. However, the quantum efficiency can be considered together with the above light attenuation factor.

A measurement method which can obtain the high measurement precision even though there is the light attenuation will be explained below. Assuming the attenuation factor of the light attenuation is $\eta$, the measurement value Q is derived from equation (1.8) to obtain, $$\ln Q[\rho] = \ln[\eta z_0/(2\pi)] - (3/2)\ln(z_o^2 + \rho^2) + \quad (1.9)$$
$$\ln[\mu_{eff}(z_o^2 + \rho^2)^{1/2} + 1] - \mu_{eff}(z_o^2 + \rho^2)^{1/2}$$

for $$z_0 = a/(\mu_a + \mu_s'). \quad (1.10)$$

Here, a is a constant which is determined experimentally or based on the experience, typically $0.3<a<3$.

The unknown values in equation (1.9) are apparently $\mu_a$, $\mu_s'$, and $\eta$, considering a is a constant. Accordingly, the photodetection distance $\rho$ which is a controllable known value is set to at least three different values, and at least three measurement values Q are obtained, and based on at least three simultaneous equations as a function of three or more kinds of Q, the three unknown values, i.e., the light attenuation factor $\eta$, the absorption coefficient $\mu_a$, and the transport scattering coefficient $\mu_s'$ can be calculated. In the present invention, the above-described basic knowledge is developed in the following application.

Figure 4:
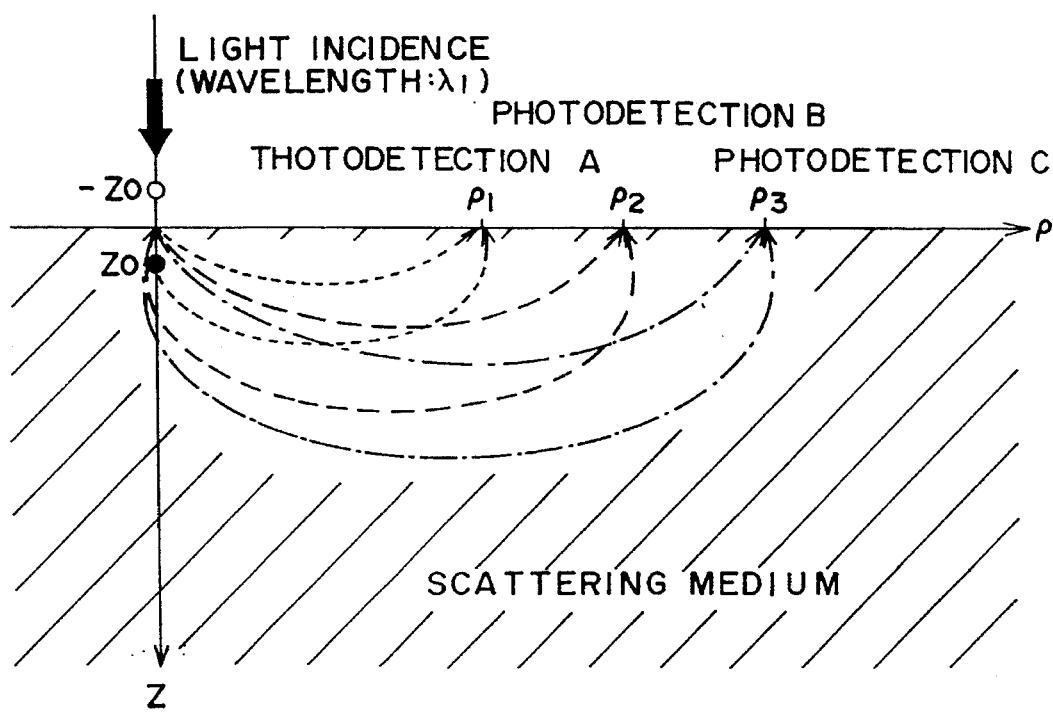
FIG. 4 is a view for explaining a principle of the present invention.

FIG. 4 is a view for explaining a method of measuring internal information in a scattering medium of the present invention. Lights are detected at three detection distances to obtain the measurement value $Q[\rho]$. Note that a distance between the light incidence position and the photodetection point is simply called a detection distance hereinafter. Three measurement values at the detection distances $\rho_1$, $\rho_2$, and $\rho_3$ are assumed to be expressed as $Q[\rho_1]$: the measurement value at the detection distance $Q[\rho_2]$: the measurement value at the detection distance $Q[\rho_3]$: the measurement value at the detection distance $\rho_3$.

Then, the three measurement values at the three kinds of the detection distances satisfy the following three simultaneous equations.

$$\ln Q[\rho_1] = \ln[\eta z_0/(2\pi)] - (3/2)\ln(z_o^2 + \rho_1^2) + \quad (1.11a)$$
$$\ln[\mu_{eff}(z_o^2 + \rho_1^2)^{1/2} + 1] - \mu_{eff}(z_o^2 + \rho_1^2)^{1/2}$$

$$\ln Q[\rho_2] = \ln[\eta z_0/(2\pi)] - (3/2)\ln(z_o^2 + \rho_2^2) + \quad (1.11b)$$
$$\ln[\mu_{eff}(z_o^2 + \rho_2^2)^{1/2} + 1] - \mu_{eff}(z_o^2 + \rho_2^2)^{1/2}$$

$$\ln Q[\rho_3] = \ln[\eta z_0/(2\pi)] - (3/2)\ln(z_o^2 + \rho_3^2) + \quad (1.11c)$$
$$\ln[\mu_{eff}(z_o^2 + \rho_3^2)^{1/2} + 1] - \mu_{eff}(z_o^2 + \rho_3^2)^{1/2}$$

The three equations constituting the simultaneous equations (1.11a) to (1.11c) (hereinafter also generally called (1.11)) are independent from each other, and the unknown values are $\mu_a$, $\mu_s'$, and $\zeta$. Therefore, the three unknown values $\mu_a$, $\mu_s'$ and $\eta$, and $\mu_{eff}$ or $z_0$ if desired can be obtained by using the three measurement values and $\rho_1$, $\rho_2$, and $\rho_3$ which are the known values or measured by another method. Note that in general, $\eta$ and $z_0$ are not needed to be obtained. To obtain $\mu_a$ and $\mu_s'$, or $\mu_{eff}$, the simultaneous equations may be of any form as long as the equations are independent from each other and derived from equation (1.6) or (1.7). When $\eta$ can be treated as a known value, $\mu_a$ and $\mu_s'$, and $\mu_{eff}$ can be obtained by solving the simultaneous equations of two equations arbitrarily from equations (1.11) or the simultaneous equations of two independent equations derived from equation (1.6) or (1.7). The computation to solve such simultaneous equations can be performed at high speed using a computer. It is apparent that the computation precision is improved as the number of independent measurement values Q is large.

Figure 5:
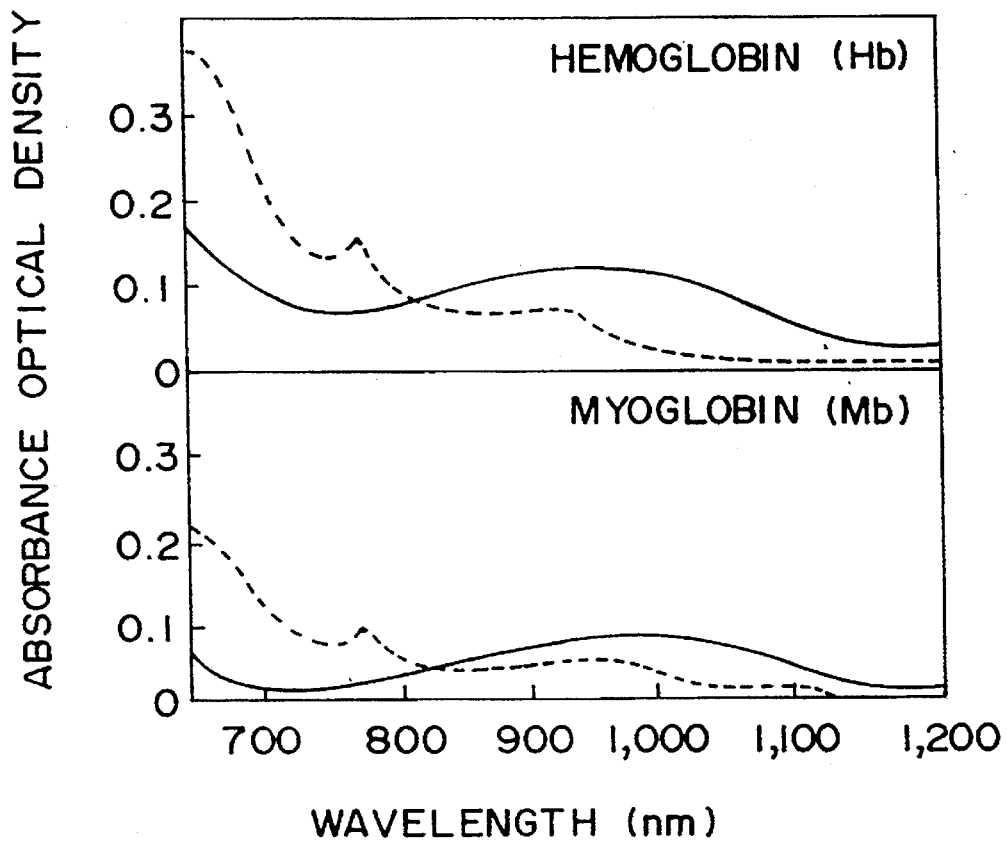
FIG. 5 is a graph showing absorption spectra of respective biological materials.

In the above-described measurement, using lights having different wavelengths $\lambda_1$ and $\lambda_2$, the absorption coefficients $\mu_{a1}$ and $\mu_{a2}$ with respect to each wavelength and the transport scattering coefficients $\mu_{s1}'$ and $\mu_{s2}'$ with respect to each wavelength can be obtained. Therefore, for example, the degree of oxygen saturation of hemoglobin is calculated from a value of $\mu_{a1}/\mu_{a2}$. In such dual-wavelength spectroscopy measurement shown in FIG. 5, wavelength dependency of the absorption coefficient of the absorptive constituents contained in the scattering medium is utilized. For example, in the measurement of oxyhemoglobin and reduced hemoglobin, or oxymyoglobin and reduced myoglobin, the spectra of which are shown in FIG. 5, light having a wavelength in which the absorption coefficient difference between oxidation and deoxidation is large, that is, light having 700 nm to 1.2 µm wavelength is frequently used.

The significant point is that in the measurement method and apparatus according to the present invention, the absolute values of the transport scattering coefficients $\mu_{s1}'$ and $\mu_{s2}'$ can be obtained. Therefore, even though the assumption on the conventional dual-wavelength spectroscopy, that is, the assumption that regardless of the similarity or difference of the scattering coefficients of the scattering constituents with respect to lights having two different wavelengths, the scattering coefficients are extremely small, does not hold, the measurement method and apparatus of the present invention can perform the measurement with high precision. As described above, the measurement method and apparatus according to the present invention can largely improve the measurement precision by expanding the application of the conventional dual-wavelength spectroscopy measurement.

The present invention utilizes the integral value of the detected optical signal, so that the incident light pulse waveform, which is of any forms, can be utilized without any problem as long as the integral time can be specified. For example, a square wave or continuous light is apparently suitable. If the measurement is performed with light having three or more wavelengths or at four or more detection distances, improvement in the measurement precision and/or measurement of specimens which have background absorption are possible. In FIG. 4, lights is detected at the three different points for one light incidence position, but a method in which light is incident on three different positions and light is detected at one photodetection point may be used. In a word, three or more kinds of the detection distances should be used.

The case that the object to be measured is a semi-infinite scattering medium has been explained; however, in practice, a finite scattering medium is mostly measured. In this case, the boundary condition should be satisfied at the surface and the outside of the scattering medium shown in FIG. 4, and the condition of photo diffusion should hold in most of lights which are diffused during propagation in the scattering medium. This condition holds when the scattering medium is considered to be sufficiently large as compared with $\rho_1$, $\rho_2$, and $\rho_3$. For example, the region in the curved lines in FIG. 4 shows a region through which most of the light passes. The presence of such a region is apparent from a spindle-shaped beam in the scattering medium reported by Sevick et al. or the results of Monte Carlo calculation.

When the thickness (z direction) of the scattering medium is not considered to be sufficiently large as compared with the photodetection distances $\rho_1$, $\rho_2$ and $\rho_3$, second point light sources of negative polarity and positive polarity which satisfy the boundary condition may be installed on the back surface (surface in opposition to light incident plane) of the scattering medium. In this case, theoretically, in order to compensate the influence of the second point light sources of negative polarity and positive polarity, third point light sources of negative polarity and positive polarity are required and further in order to compensate the influence of the third point light sources, fourth point light sources of negative polarity and positive polarity are required. However, since the influence of the installed point light sources to the emitted light rapidly decreases in order, the influence can be approximated by finite point light sources. In this case, the above-stated equations (1.5 to (1.9) are required to be modified by adding terms related to the influence of the additional point light sources of negative polarity and positive polarity. However, since this modification only increases the number of terms, and does not change the number of unknown values nor the independence of every equation, the same relation as described above can hold.

Figure 6:
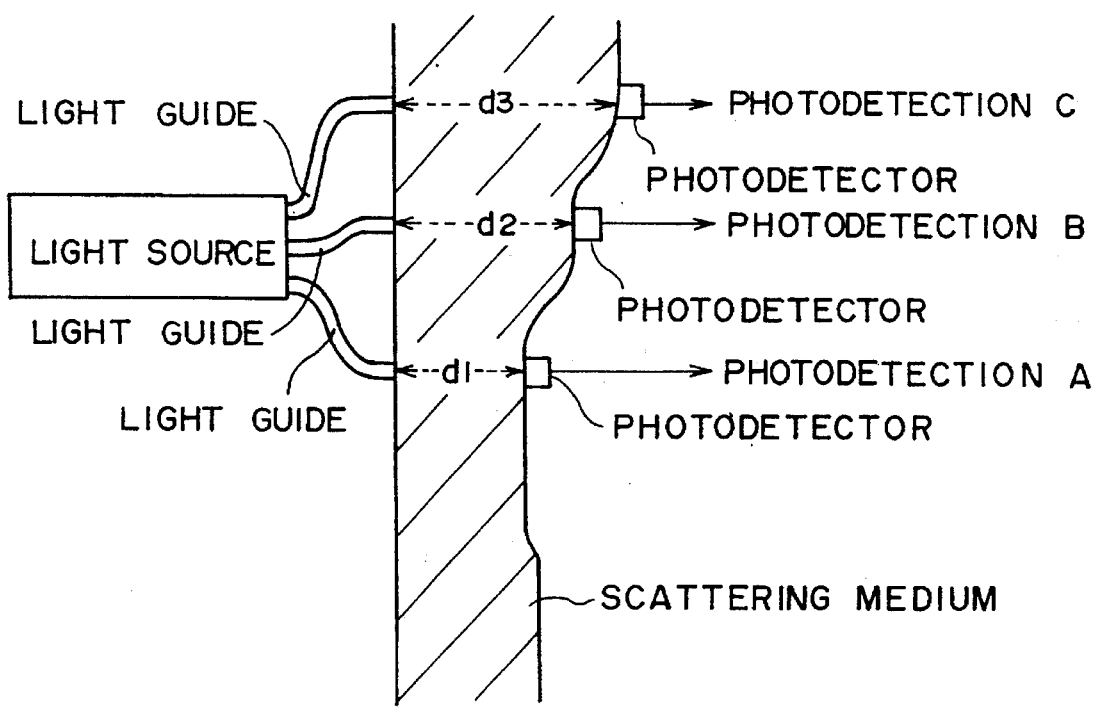
FIG. 6 is a view showing principle of measurement of as lab-like specimen.

The measurement method and apparatus of the present invention can also be applied to a slab-like specimen, and its state is shown in FIG. 6. Light is incident on three points in FIG. 6, but light may be incident on one point and lights are detected at three points of different detection distances. In the case of the slab-like specimen, assuming the detection distance is d, a result derived from the photon diffusion equation (1.3) which is equivalent to the above-stated equation (1.7) is, for example, $$I[d] = \exp(-d\mu_{\text{eff}})/(2\pi d^3) \times \qquad (1.12)$$
$$\{(1 + 3z_0/d)[\mu_{\text{eff}}(d - z_0) + 1](d - z_0)\exp(z_0\mu_{\text{eff}}) - $$
$$(1 - 3z_0/d)[\mu_{\text{eff}}(d + z_0) + 1](d + z_0)\exp(-z_0\mu_{\text{eff}})\}$$

The equation which is equivalent to equation (1.9) becomes $$Q[d]=\eta I[d]. \qquad (1.13)$$

However, these equations are modified forms of equations (1.7) and (1.9), that is, the number of unknown values and the number of known values remain the same, and the parameters are also the same, so that similar to the above case, the arithmetic operation is conducted and the same results as the above case can be obtained. Therefore, in the same way as described above, the three unknown values $\mu_a$, $\mu_s'$ and $\eta$, and also $\mu_{\text{eff}}$ if needed can be obtained with use of the three measured values and the known values $\rho_1$, $\rho_2$, and $\rho_3$. Note that in general it is not necessary to obtain, $\eta$ and $z_0$. When $\eta$ is the known value, $\mu_a$, $\mu_s$, and $\mu_{\text{eff}}$ can be obtained from the simultaneous equations of arbitrary two independent equations. Further, the internal information relating to absorptive constituents such as the degree of oxygen saturation of hemoglobin can be obtained. In the same way as described above, the computation to solve the simultaneous equations is performed at high speed using a computer.

Further, the internal information in the scattering medium as described above is a mean value of information along with the optical path of light which is diffused during propagation to the photodetection point from the light incidence position. Therefore, when the internal information is coarsely diffused enough as compared with the distance between the light incidence position and the photodetection point as shown in FIG. 4, or as compared with the interval of the light incidence positions, the spatial distribution of various kinds the measurement values can be imaged, that is, a simple imaging technique. It is apparent that if the above-described measurement is performed at different times, the time change in the internal information can be measured, and it is applied to the measurement or monitoring for the amount of oxygen in the brain or other tissues. In these cases, the imaging and the computation can be performed at high speed using a computer unit which comprises a memory, a display or others.

Errors in measurement in both cases of a method of the present invention and a conventional absorption method in which the optical pathlength is assumed to be a constant will be explained to show one example of the effectiveness of the present invention. Considering the scattering medium which occupies infinite spaces as shown in FIG. 4, the optical signal to be detected is expressed by equation (1.5). The average optical pathlength $<L>$, that is, the centroide of time-resolved waveform is considered for such a signal to obtain, $$<L>=[c\int_0^\infty tR(\rho,0,t)dt]/[\int_0^\infty R(\rho,0,t)dt]=(3/2)(\mu_a+\mu_s')(z_0^2+\rho^2)/[1+(z_0^2+\rho^2)^{1/2}\mu_{\text{eff}}]. \qquad (1.14)$$

Assuming that $\mu_s'=0.45[\text{mm}^{-1}]$, $z_0=1/\mu_s'$ as typical values for the living body specimen, and that $\rho=50[\text{mm}]$ as the measurement condition, and that the average optical pathlengths are $<L(\mu_a=0.01)>$ and $<L(\mu_a=0.02)>$, when $\mu_a$ is changed from 0.01 to 0.02, respectively, and the optical pathlength is constant, error $\Delta$ in the average optical pathlength is given by $$\Delta=\{<L(\mu_a=0.01)>-<L(\mu_a=0.02)>\}/<L(\mu_a=0.02)>\times 100\approx 14(\%). (1.15)$$

Consequently, the absorbance optical density obtained under the assumption of the optical pathlength be the constant has about 14% error. To the contrary, the method and apparatus of the present invention perform the arithmetic processing utilizing the relation in which the change of the optical pathlengths is taken into consideration, so that the errors as described above can be eliminated. The above description is the same in the case of the measurement of the slab-like scattering medium, and there is small difference in the percentage of errors, but the effectiveness of the present invention is apparent.

(1.2) Measurement Method of Absorption Information

A method in which information relating to absorptive constituents is processed and extracted with use of the absorption coefficient obtained as described above will be explained below.

(i) Measurement Method of Degree of Oxygen Saturation of Hemoglobin

Main absorptive constituents in a mammalian brain are water, cytochrome, oxyhemoglobin, and reduced hemoglobin. Absorption of water and cytochrome in a near-infrared range is as small as negligible with respect to an oxyhemoglobin and a reduced hemoglobin. The oxyhemoglobin and the reduced hemoglobin have different absorption spectra, as shown in FIG. 5. The skull is regarded as a scattering medium with respect to near-infrared rays.

The two kinds of lights having wavelengths $\lambda_1$ and $\lambda_2$ are considered. Absorption coefficients corresponding to the wavelengths $\lambda_1$ and $\lambda_2$ can be obtained in accordance with the Lambert-Beer law as follows:

$$\mu_{a1} = \epsilon_{Hb,1}[Hb] + \epsilon_{HbO,1}[HbO] \tag{2.1a}$$

$$\mu_{a2} = \epsilon_{Hb,2}[Hb] + \delta_{HbO,2}[HbO] \tag{2.1b}$$

where $\delta_{Hb,1}$: the molar absorption coefficient [mm$^{-1}$·M$^{-1}$] of the reduced hemoglobin at the wavelength $\lambda_1$ $\epsilon_{HbO,1}$: the molar absorption coefficient [mm$^{-1}$·M$^{-1}$] of the oxyhemoglobin at the wavelength $\lambda_1$ $\epsilon_{Hb,2}$: the molar absorption coefficient [mm$^{-1}$·M$^{-1}$] of the reduced hemoglobin at the wavelength $\lambda_2$ $\epsilon_{HbO,2}$: the molar absorption coefficient [mm$^{-1}$·M$^{-1}$] of the oxyhemoglobin at the wavelength $\lambda_2$

[Hb]: the molar concentration [M] of the reduced hemoglobin

[HbO]: the molar concentration [M] of the oxyhemoglobin

Since the degree Y of oxygen saturation is given by $$Y = [HbO]/([Hb] + [HbO]), \tag{2.2}$$

the following equation is obtained.

$$\mu_{a1}/\mu_{a2} = [\epsilon_{Hb,1} + Y(\delta_{HbO,1} - \epsilon_{Hb,1})]/[\epsilon_{Hb,2} + Y(\epsilon_{HbO,2} - \epsilon_{Hb,2})] \tag{2.3}$$

Therefore, the molar concentration of the reduced hemoglobin [Hb], the molar concentration of the oxyhemoglobin [HbO], the molar concentration of the hemoglobin [Hb]+[HbO] and the degree Y of oxygen saturation are calculated using $\mu_{a1}$ and $\mu_{a2}$, or $\mu_{a1}/\mu_{a2}$ obtained from the above measurement, and the known parameters $\epsilon_{Hb,1}$, $\epsilon_{HbO,1}$, $\epsilon_{Hb,2}$, and $\epsilon_{HbO,2}$. If a wavelength ($\approx$800 nm, isosbestic wavelength) which has the same absorption level for both an oxyhemoglobin and a reduced hemoglobin is used, the above equation can be made simpler.

(ii) Presence of Background Absorption

Background absorption may not be neglected in a living body. In this case, if the background absorption levels at the wavelengths $\lambda_1$, $\lambda_2$, and $\lambda_3$ are defined as $a_1$, $a_2$, and $a_3$, respectively, the following equations are established in accordance with the Lambert-Beer law.

$$\mu_{a1} = \epsilon_{Hb,1}[Hb] + \epsilon_{HbO,1}[HbO] + a_1 \tag{2.4a}$$

$$\mu_{a2} = \epsilon_{Hb,2}[Hb] + \epsilon_{HbO,2}[HbO] + a_2 \tag{2.4b}$$

$$\mu_{a3} = \epsilon_{Hb,3}[Hb] + \epsilon_{HbO,3}[HbO] + a_3 \tag{2.4c}$$

The above equations are rearranged to obtain the following equation:

$$(\mu_{a1} - \mu_{a2})/(\mu_{a3} - \mu_{a2}) = [(\epsilon_{Hb,1} - \epsilon_{Hb,2}) + Y(\epsilon_{HbO,1} - \epsilon_{HbO,2} - \epsilon_{Hb,1} + \epsilon_{Hb,2}) + K(a_1 - a_2)] \div [(\epsilon_{Hb,3} - \epsilon_{Hb,2}) + Y(\epsilon_{HbO,3} - \epsilon_{HbO,2} - \epsilon_{Hb,3} + \epsilon_{Hb,2}) + K(a_3 - a_2)] \tag{2.5}$$

$$\text{for } K = 1/([Hb] + [HbO]). \tag{2.6}$$

Therefore, if the wavelengths are suitably selected so that $a_1 \approx a_2 \approx a_3$, in the same way as described above, [Hb], [HbO], [Hb]+[HbO], and the degree Y of saturation can be obtained by obtaining $\mu_{a1}$, $\mu_{a2}$ and $\mu_{a3}$ using the measurement values at the lights having three wavelengths and the known parameters, and substituting $\mu_{a1}$, $\mu_{a2}$, $\mu_{a3}$ and the known parameters into equation (2.4) or equation (2.5). Note that the above condition $a_1 \approx a_2 \approx a_3$ can be achieved by properly selecting a wavelength for the object to be measured such as a living body.

Figure 7:
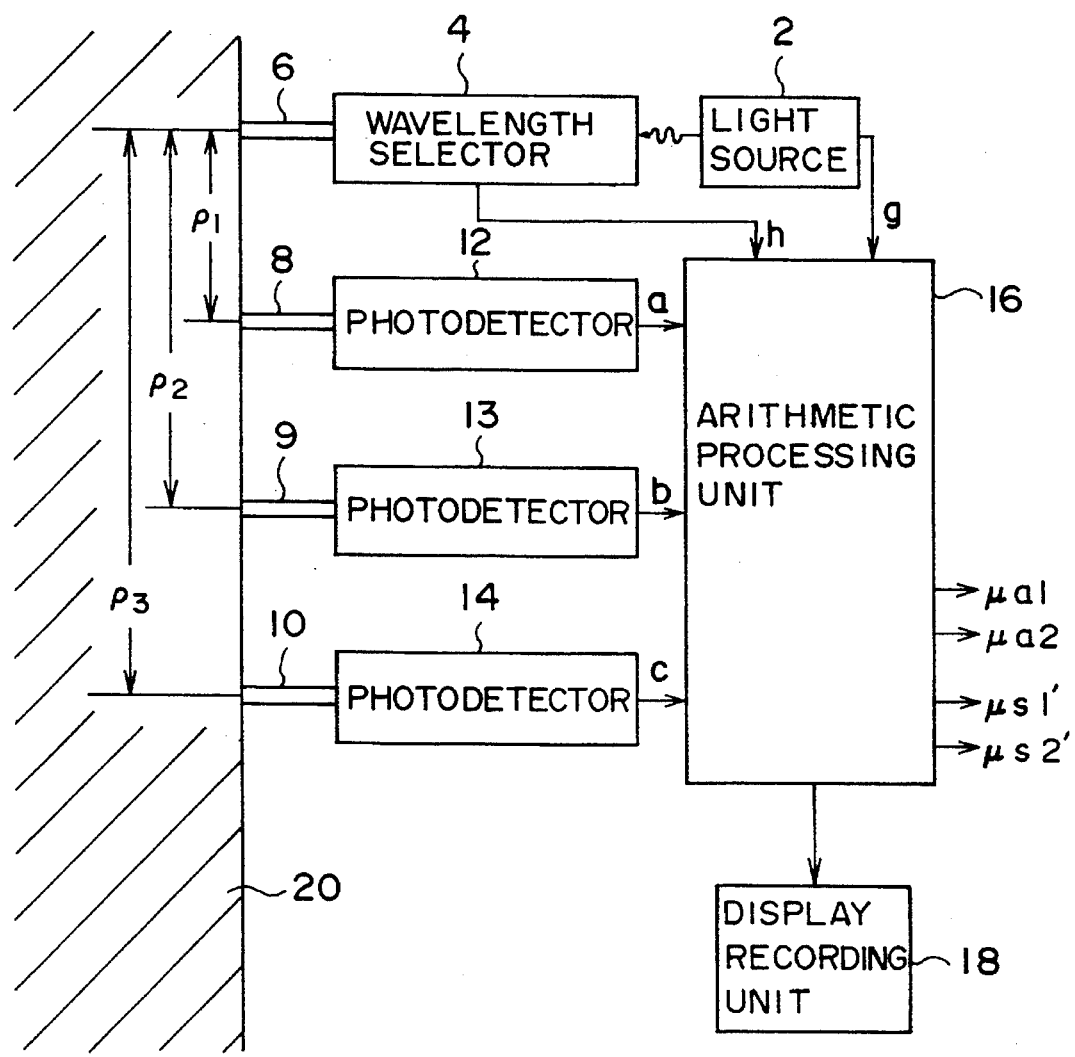
FIG. 7 is a view showing a configuration of an apparatus of the first embodiment.

(2) Apparatus for Measuring Internal Information in Scattering Medium (2.1) First Embodiment of the Apparatus The first embodiment of the apparatus carrying out the method of measuring internal information in a scattering medium according to the present invention is shown in FIG. 7. A light source 2 using a laser diode or the like generates lights having certain wavelengths $\lambda_1$ and $\lambda_2$. The wavelength of light from the light source must be appropriately selected in accordance with an object to be measured. Light having a wavelength of 700 [nm] or more is generally preferable in association with absorption of a hemoglobin or the like. Since the oxyhemoglobin and the reduced hemoglobin have different absorption coefficients, as shown in FIG. 5, the oxyhemoglobin is distinguished from the reduced hemoglobin by selecting an appropriate wavelength and then measured. Various kinds of light sources such as a light emitting diode, a laser diode, a HeNe laser or others can be used. Further, the light source which generates pulsed light or square wave light as described above may be used.

A wavelength of light from the light source 2 is selected by a wavelength selector 4 and the light is incident on a surface of a scattering medium 20 which is an object to be measured through a light guide 6. In this case, there is another method utilizing a condenser lens or a pinhole, which will be described later. Since the average diffusion length is approximately 2 [mm] in the scattering medium such as the living body specimen as described above, the incident light is scattered before it propagates about 2 [mm], and loses the original direction. Therefore, the influence of the average diffusion length in a few cm scattering medium can be neglected, so that spot-like light must be caused to be incident on the scattering medium. Thick beam-like light may be caused to be incident on the scattering medium. This case is considered as a plurality of linear spot-like light sources.

A space between the light guide 6 and the object 20 to be measured is very small in the embodiment of FIG. 7. However, this can be made large, and a liquid medium or a jelly-like object (hereinafter called an interface material) having substantially the same refractive index and scattering coefficient as the scattering medium 20, which is the object to be measured, may be filled in this space. Since the light is diffused during propagation in the interface material and then incident on the object to be measured, no problems arise. If the surface reflection on the scattering medium is a problem, the influence of the surface reflection or others can be reduced by properly selecting the interface material.

The light diffused during propagation in the scattering medium 20 is received by light guides 8, 9 and 10 provided at positions spaced apart from the light incident position by distances $\rho_1$, $\rho_2$, and $\rho_3$, respectively. The interface material may also be used for the same reasons as described above.

The first photodetector 12, the second photodetector 13, and the third photodetector 14 convert the received optical signals into electric signals, amplify the signals and output the detected signals a, b, and c, respectively. Various kinds of photodetectors such as a photomultiplier, a phototube, a photodiode, an avalanche photodiode, or a PIN photodiode can be used as the photodetectors 12, 13, and 14. Any photodetector can be selected as long as it has spectral sensitivity that allows it to detect light having the specified wavelength. If an optical signal is very feeble, a high-sensitivity and high-gain photodetector is used. The other parts of the photodetector other than the light incident plane may preferably have the structure which absorbs or shields light. If light diffused during propagation in the scattering medium has light components having a plurality of wavelengths, a wavelength selection filter (not shown) is inserted between the photodetectors 12, 13, and 14 and the scattering medium 20.

An arithmetic processing unit 16 processes the detected signals a, b and c from the first detector 12, the second detector 13, and the third detector 14, and converts the signals a, b, and c into the measurement values d, e and f in proportion to the detected quantity of light, respectively. In particular, the arithmetic processing unit 16 integrates the detected signals a, b, and c in time by utilizing a signal g which synchronizes with the light generation of the light source 12 to calculate the measurement values d, e, and f in proportion to the detected quantity of light. Note that when the pulsed light is utilized, the synchronized signal g may be omitted. Next, the measurement values d, e and f, and the known parameters $\rho_1$, $\rho_2$, and $\rho_3$ which are set or measured by another method are processed based on the three simultaneous equations corresponding to the wavelengths $\lambda_1$, and $\lambda_2$ to calculate the absorption coefficients and the transport scattering coefficients corresponding to the wavelengths $\lambda_1$ and $\lambda_2$, i.e., $\mu_{a1}$ and $\mu_{s1}'$, and $\mu_{a2}$ and $\mu_{s2}'$. This sort of arithmetic processing can be operated at high speed by a micro computer installed in the arithmetic processing means. If desired, the concentration of the specified absorptive constituents is calculated by using the obtained internal information, i.e., $\mu_{a1}$ and $\mu_{a2}$. If background absorption is present, the lights having three or more kinds of wavelengths as described above are used.

Figure 8:
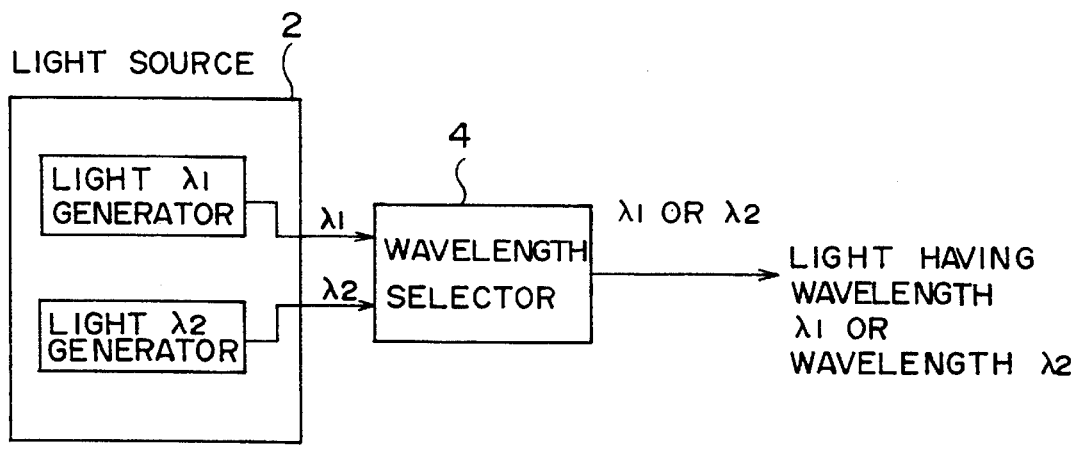
FIGS. 8 and 9 are views respectively showing a configuration of switching and mixing lights having different wavelengths.
Figure 9:
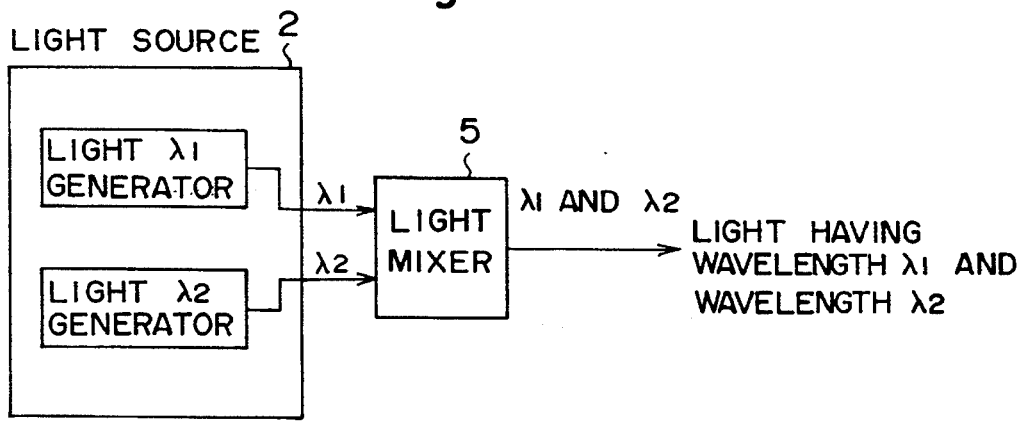
Figure 10:
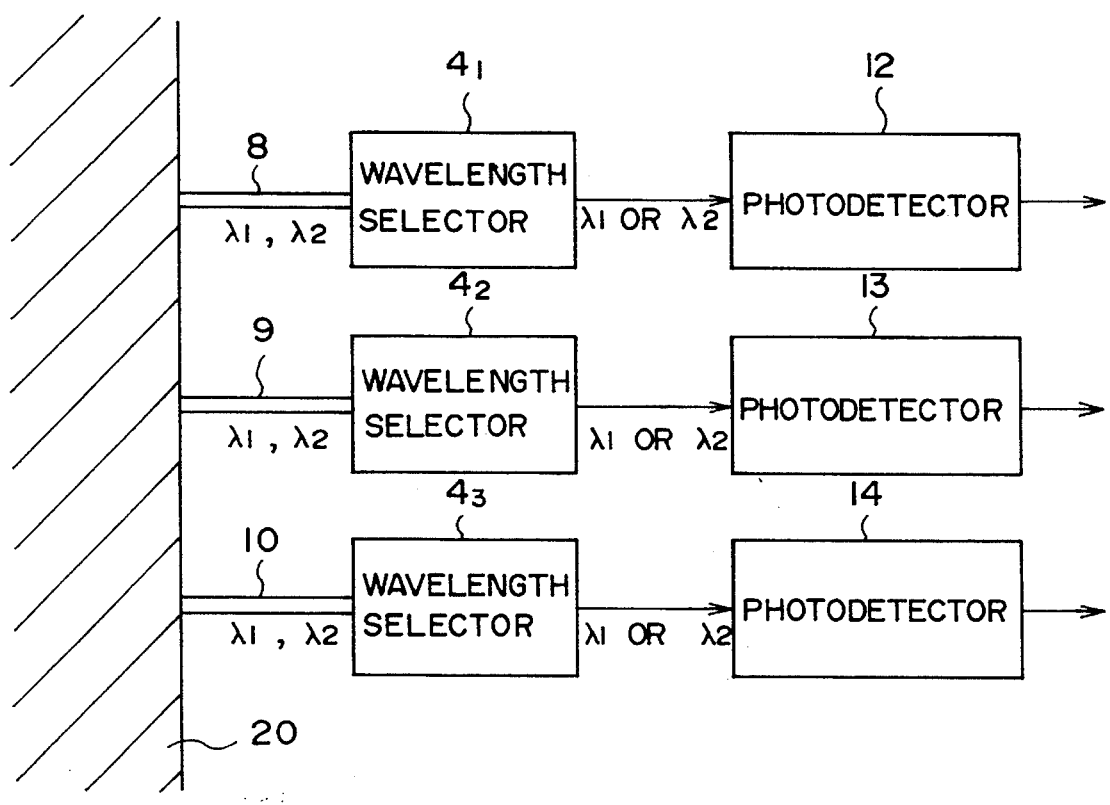
FIG. 10 is a view showing a configuration of performing detection of lights having different wavelengths.

In the above case, there is a method using time-divided light having a different wavelength emitted, and a method using light having different wavelengths at the same time. As means for selecting a wavelength, there is a method (FIG. 8) utilizing a light beam selector using a mirror, a method using a wavelength selector using a filter, or a method using a light selector using an optical switch. In addition, a method of selecting a wavelength by a wavelength selection filter provided in front of a light incident position with lights having different wavelengths being formed into a coaxial beam, a method of causing lights having different wavelengths to be incident on the scattering medium in parallel (FIG. 9) and selecting a wavelength by a wavelength selection filter provided in front of the photodetector (FIG. 10), and further a method of detecting lights having two kinds of wavelengths at a respective detection point using six photodetectors, and a method of properly combining these methods, are available.

Figure 11:
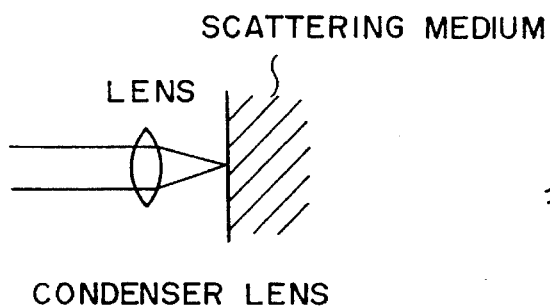
FIGS. 11–14 are views respectively showing a method of causing light to be incident on a scattering medium.
Figure 12:
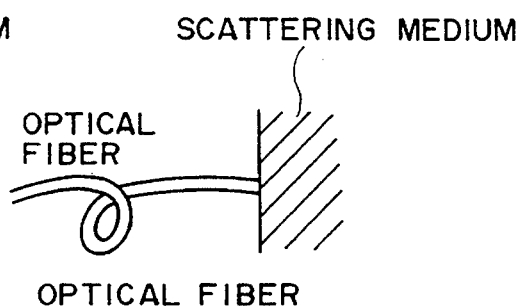
Figure 13:
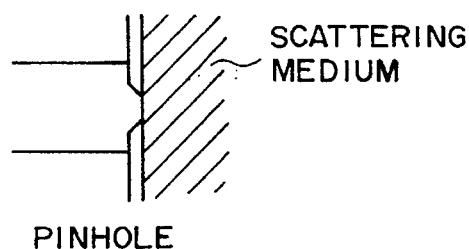
Figure 14:
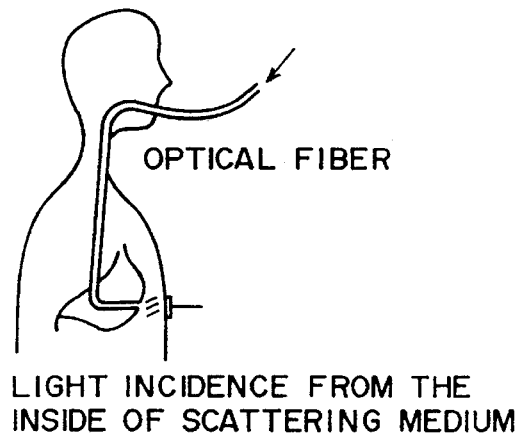
Figure 15:
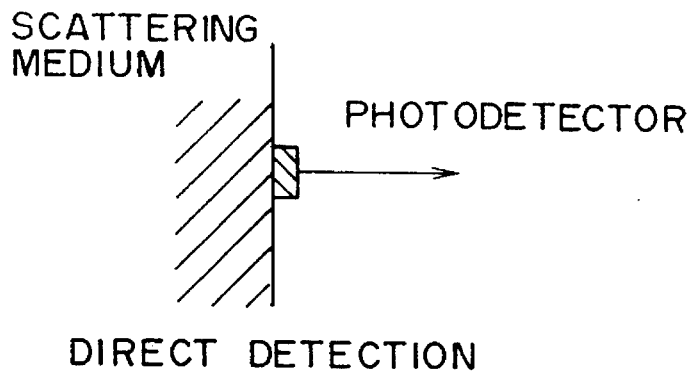
FIGS. 15–17 are views respectively showing a method of receiving light.
Figure 16:
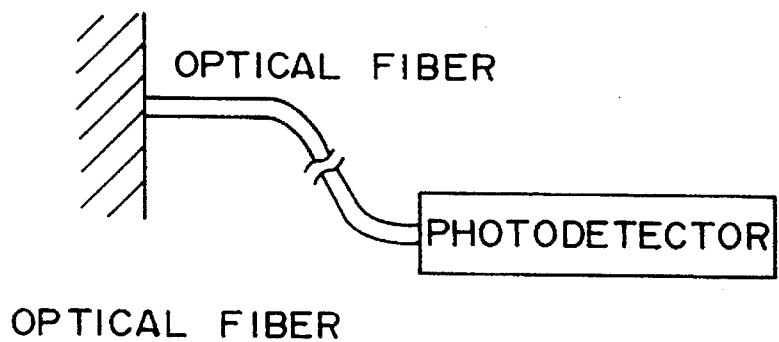
Figure 17:
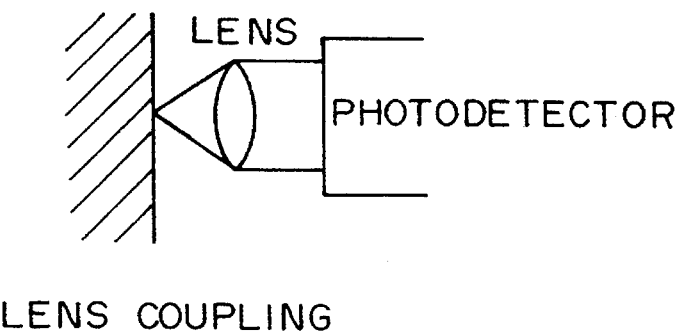

A means for causing the light to be incident on a scattering medium such as a living body may be constituted by a method utilizing a condenser lens (FIG. 11), an optical fiber (FIG. 12), or a pinhole (FIG. 13), or a light incident method using a gastro camera (FIG. 14) or the like, other than the method using light guides as shown in FIG. 7. A means for receiving and detecting the light propagating through the scattering medium may be constituted by a direct photodetection method (FIG. 15), a method of detecting the light through an optical fiber (FIG. 16), a method of detecting light through a lens (FIGS. 17), or the like.

Figure 18:
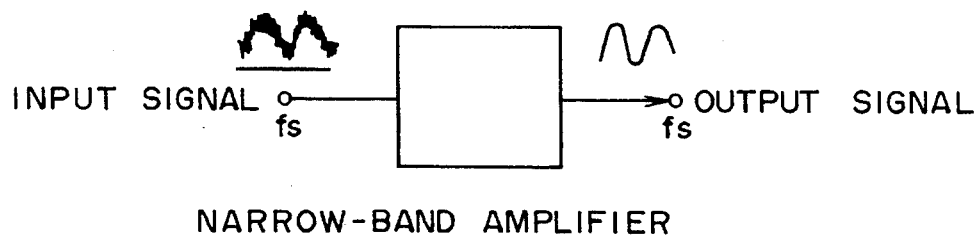
FIGS. 18 and 19 are views respectively showing a method of amplifying a detected signal with low noise.
Figure 19:
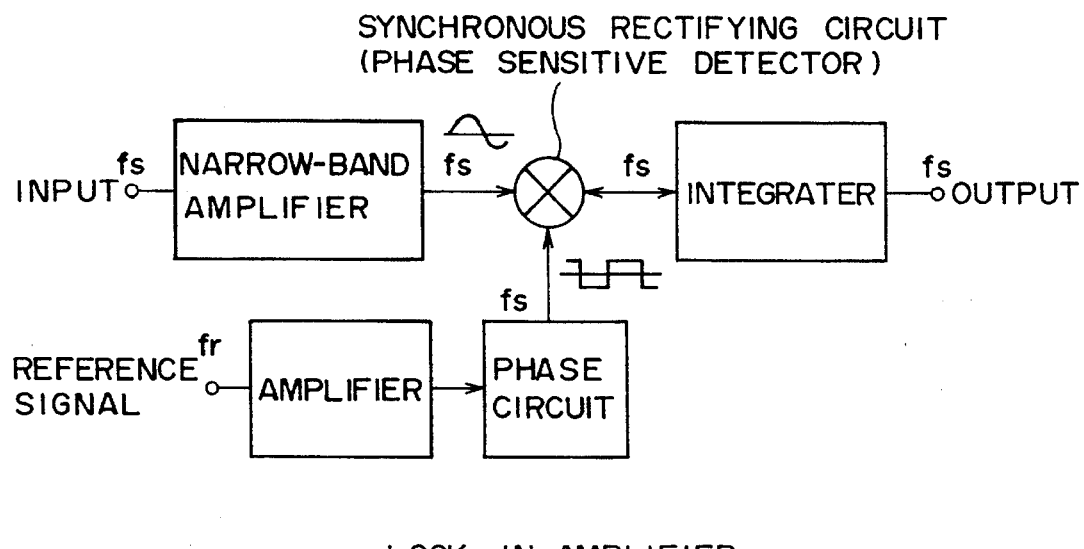

If the signal detected by the photodetector is required to be amplified with low noise, a narrow-band amplifier (FIG. 18), a lock-in amplifier (FIG. 19) or the like can be used. When the lock-in amplifier is used, as a reference signal, the aforementioned synchronizing signal g is utilized. This method is effective for the measurement of a high dynamic range using square wave light or pulsed light. If the absorptive layer is present on the surface of the scattering medium 20 such as a living body specimen, the measurement values d, e and f can be compensated using the absorption values measured at the position of the detection distances $\rho_1$, $\rho_2$ and $\rho_3$.

The light incident position and the photodetection points on the scattering medium are concurrently scanned (not shown), and internal information of every location of the scattering medium is obtained and accumulated in a frame memory (not shown), and then read by a TV system, whereby the image showing distribution of internal information can be obtained. If the measurement is performed at a different time, the time-change in internal information can be measured. The arithmetic processing unit 16 has a function of storing the thus obtained internal information, and a display recording means 18 shown in FIG. 7 displays and/or records the course of processing and these results. The arithmetic processing can be operated at high speed by a computer unit comprising a memory, a display, etc.

Moreover, the same measurement can be made to the slab-like specimen as described above. In this case, the light incident position and photodetection points are required to be provided on a surface opposing the scattering medium and set on the different detection distances so as to detect the transmitted Light diffused during propagation as shown in FIG. 6.

(2.2) Second Embodiment of the Apparatus

Figure 20:
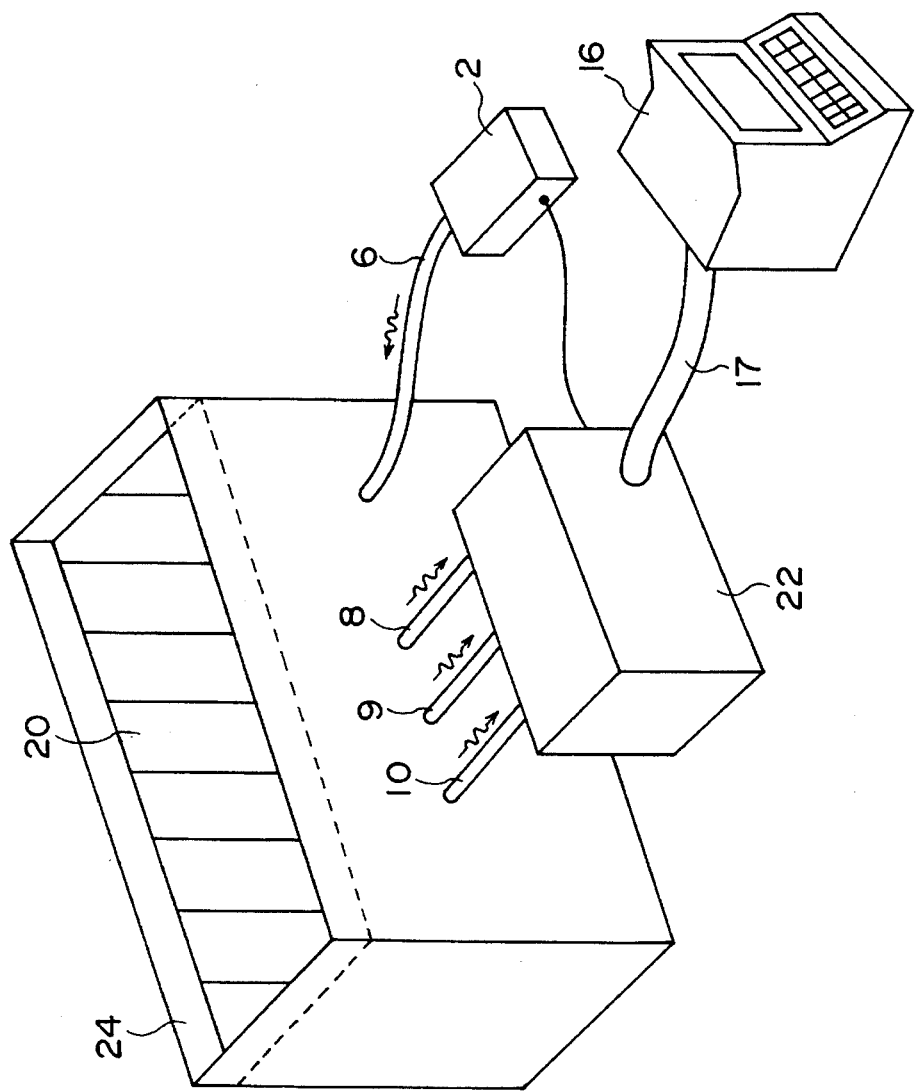
FIG. 20 is a view showing a configuration of an apparatus of the second embodiment.

The second embodiment of the apparatus carrying out the method of measuring internal information in a scattering medium according to the present invention is shown in FIG. 20. This apparatus is for the measurement of the optical constants in the scattering medium, and the specimen 20 put in a container 24 is a scattering medium, and its absorption coefficient and its transport scattering coefficient are unknown. The apparatus of this embodiment uses light having a predetermined wavelength, and its operation is substantially the same as the first embodiment except for use of dual-wavelengths. In FIG. 20, the parts which has the same function as described in FIG. 7 are represented by the same reference numerals.

Light having a predetermined wavelength from a light source 2 is incident on a liquid specimen 20 which is put in the container 24 through a light guide 6. Light propagated during propagation in the specimen which is an object to be measured is received by light guides 8, 9 and 10 placed at positions spaced apart from the light incident position by distances $\rho_1$, $\rho_2$ and $\rho_3$, converted into the detected signals a, b and c by a photodetector (not shown) provided in a detecting unit 22, and provided to an arithmetic processing unit 16 in the next stage. The arithmetic processing unit 16 processes the detected signals a, b and c, and converts the signals into the measurement values d, e and f in proportion to the detected quantity of light, respectively. Next, the measurement values d, e and f, and known parameters $\rho_1$, $\rho_2$ and $\rho_3$ measured or set by another method are processed based on the simultaneous equations as described above to calculate the scattering coefficient $\mu_{a1}$ and the transport scattering coefficient $\mu_{s1}'$ of the scattering medium. This sort of the arithmetic processing is operated at high speed by a microcomputer installed in the arithmetic processing unit 16.

In the above case, a light source, a light incident means, and a photodetecting means, an amplifying means for a detected optical signal as described in the first embodiment can be utilized. These apparatuses are meant to measure the optical constants of an unknown scattering medium and are used for general purpose, in various fields such as science and engineering, biology, spectral analysis, and others.

(2.3) Third Embodiment

Figure 21:
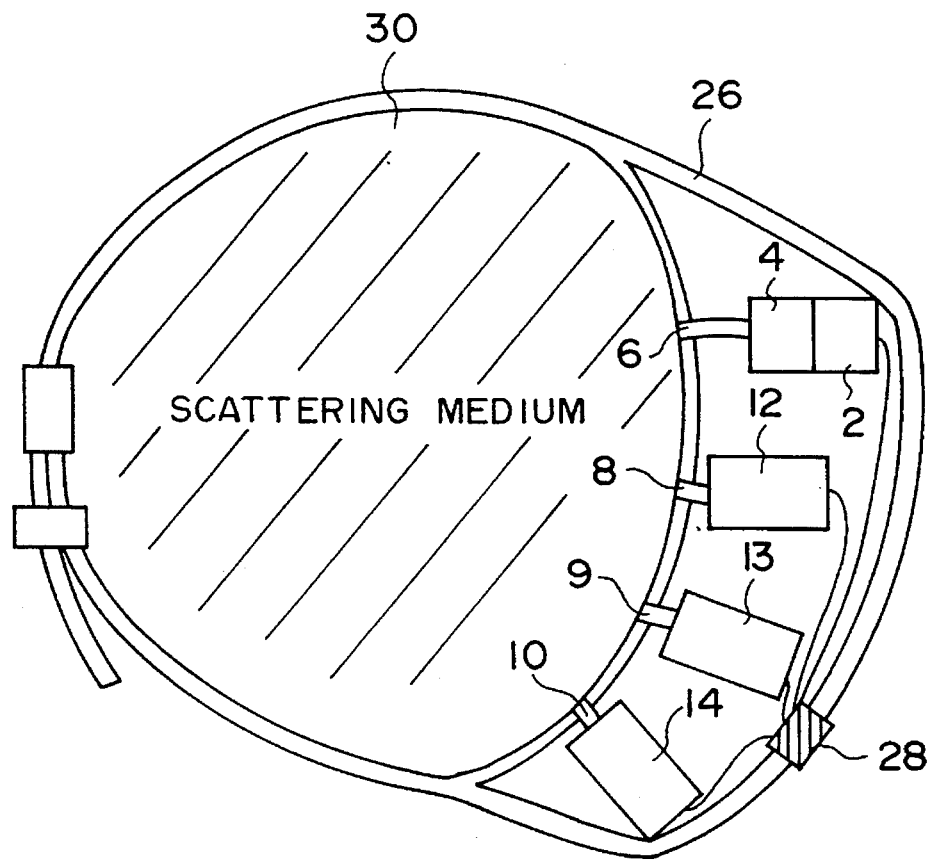
FIG. 21 is a view showing a configuration of a main part of an apparatus of the third embodiment.

The third embodiment of the apparatus carrying out the method of measuring internal information in a scattering medium according to the present invention is shown in FIG. 21. This apparatus is for the measurement and/or the monitoring of the concentration of oxyhemoglobin or the degree of oxygen saturation of hemoglobin in a human brain. A band-type container 26 is put on a head 30 like a headband to measure the degree of saturation of hemoglobin in a brain. The apparatus of this embodiment uses light having two predetermined wavelengths $\lambda_1$ and $\lambda_2$, and the operation is substantially the same as the first embodiment. In FIG. 21, the parts each which has the same function as described in FIG. 7 are represented by the same reference numerals.

The wavelengths of the light having two different wavelengths $\lambda_1$ and $\lambda_2$ are selected by a wavelength selector 4, and light is incident on the head 30 which is an object to be measured through a light guide 6. The two wavelengths should be properly selected. Light diffused during propagation in the head which is an object to be measured is received by light guides 8, 9 and 10 arranged at positions spaced apart from the light incidence position by distances $\rho_1$, $\rho_2$, and $\rho_3$, and converted and amplified into electric signals by the first photodetector 12, the second photodetector 13 and the third photodetector 14. In this case, a power supply, or a signal is coupled to external equipment (not shown) through a connector 28 installed in a container 26. The arithmetic processing (not shown) of signals is the same as the first embodiment, and in this embodiment, the degree of oxygen saturation of hemoglobin is displayed. In addition, the signals may be converted into electric waves or optical signals and then transmitted.

Figure 22:
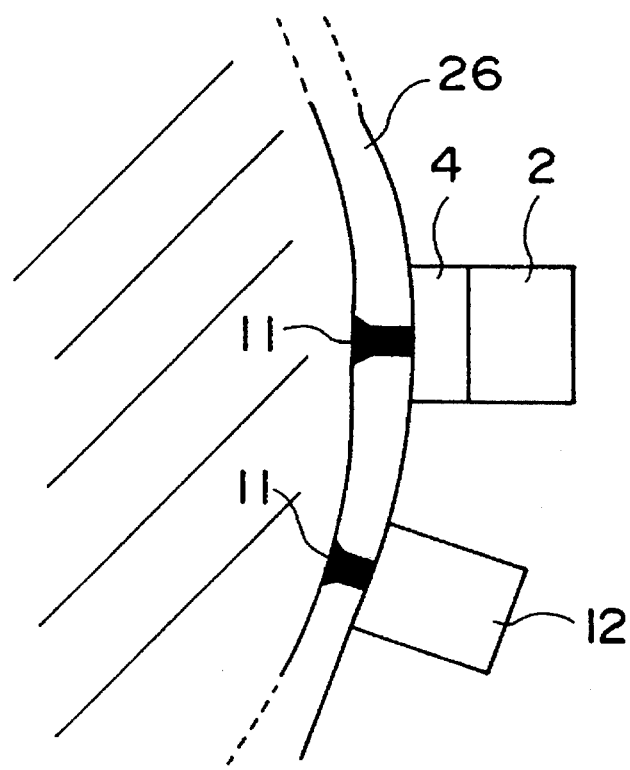
FIG. 22 is a view showing a detailed configuration a light incidence position and a photodetection point.

A light source, a light incidence means, a photodetecting means, and an amplifying means for the detected optical signals as described in the first embodiment can be utilized. Surface reflection or a space between the light guide and the head may be a problem for the human head. In this case, the interface material may be utilized as described above. FIG. 22 shows a modified example of a Light incident position and a detector shown in FIG. 21 in detail. In this example, light guides shown in FIG. 21 are omitted, and the interface material 11 having substantially the same scattering coefficient and the absorption coefficient as an object to be measured is used in a space between a head and a wavelength selector 4, and a space between a head and a photodetector 12. In this way, a difference in the state of the light coupling between photodetection at $\rho_1$, $\rho_2$ and $\rho_3$ and the head can be reduced, and efficiency of light collection is improved.

These apparatuses can be used, e.g., for the measurement or the monitoring of the concentration of oxyhemoglobin in a muscle of a human who runs a marathon.

As described above, according to the method of measuring internal information in the scattering medium and the apparatus for the same, the measurement of the internal information in the scattering medium at high precision is possible. That is, the absolute values of the transport scattering coefficient $\mu_s'$ and the absorption coefficient $\mu_a$ can be measured. If the principle of the dual-wavelength spectroscopy is further utilized, the internal information such as the concentration of the specified constituent can accurately be measured. The spatial distribution and time-change in the internal information can be measured. Moreover, since the measurement apparatus which utilizes the present invention uses the time-integrated value of the optical signal, to light utilization factor is high, and as the signal-to-noise ration is large, the measurement precision becomes high. Therefore, the non-invasive measurement and imaging for the internal information of a human head, a body, a plant such as a standing tree, or other types of living tissue can be operated by a simple apparatus.

What is claimed is:

1. A method of measuring a scattering medium comprising:

emitting light having a single predetermined wavelength;

causing said light to be incident on the scattering medium at a light incidence position to allow said light to propagate through the scattering medium;

detecting said light which has propagated through the scattering medium at at least three photodetection points, with distances, $\rho_i$, between the light incidence position and each of the photodetection points being different from each other, to obtain at least three detected signals; and extracting internal information of the scattering medium with respect to said wavelength of said light, by converting said at least three detected signals to at least three measured values, $Q(\rho_i)$, and then performing arithmetic processing to said at least three measured values, $Q(\rho_i)$, based on a simultaneous relation of the following equation:

$$\ln Q(\rho_i) = \ln (\eta z_0/2\pi) - \frac{3}{2} \ln (z_0^2 + \rho_i^2) + \ln (\mu_{\mathit{eff}}(z_0^2 + \rho_i^2)^{1/2} + 1) - \mu_{\mathit{eff}} \sqrt{(z_0^2 + \rho_i^2)}$$

for $z_0 = a/(\mu_a + \mu_s')$ where i is an integer running from one to at least three, $\eta$ is a light attenuation factor, $\mu_{\mathit{eff}}$ is an effective attenuation coefficient $$\mu_{\mathit{eff}} = \sqrt{(3\mu_a(\mu_a + \mu_s'))} \quad ,$$

a is a constant determined in accordance with a type of the scattering medium, $\mu_a$ represents an absorption coefficient, and $\mu_s'$ is a transport scattering coefficient.

2. A method of measuring a scattering medium according to claim 1, wherein said extracting step includes extracting internal information selected from the group consisting of $\mu_a$, $\mu_s'$, $\mu_{eff}$, $\eta$ and $z_0$.

3. A method of measuring a scattering medium according to claim 1, wherein said emitting step includes emitting light having a pulse shape, and said extracting step includes measuring light intensity as said measured values.

4. A method of measuring a scattering medium according to claim 1, wherein said detecting step includes measuring said at least three detected signals for a period of time and said extracting step includes integrating said at least three detected signals over said period of time to calculate said at least three measured values, $Q(\rho_i)$.

5. A method of measuring a scattering medium comprising:

emitting light having at least two predetermined wavelengths of which absorption coefficients to specified absorptive constituents in said scattering medium differ from one another;

causing said light to be incident on the scattering medium at a light incidence position to allow said light to propagate through the scattering medium;

detecting said light which has propagated through the scattering medium at at least three photodetection points, with distances, $\rho_i$, between the light incidence position and each of the photodetection points differing from one another, to obtain at least three detected signals with respect to each of said wavelengths of said light; and extracting internal information of the scattering medium with respect to each of said wavelengths of said light, by converting said at least three detected signals to at least three measured values, $Q(\rho_i)$, and then performing arithmetic processing to said at least three measured values, $Q(\rho_i)$, based on a simultaneous relation of the following equation:

$$\ln Q(\rho_i) = \ln (\eta z_0/2\pi) - \frac{3}{2} \ln (z_0^2 + \rho_i^2) + \ln (\mu_{eff}(z_0^2 + \rho_i^2)^{1/2} + 1) - \mu_{eff}\sqrt{(z_0^2 + \rho_i^2)}$$

for $z_0 = a/(\mu_a + \mu_s')$ where i is an integer running from one to at least three, $\eta$ is a light attenuation factor, $\mu_{eff}$ is an effective attenuation coefficient $$\mu_{eff} = \sqrt{(3\mu_a(\mu_a + \mu_s'))} \quad,$$

a is a constant determined in accordance with a type of the scattering medium, $\mu_a$ is an absorption coefficient, and $\mu_s'$ is a transport scattering coefficient.

6. A method of measuring a scattering medium according to claim 5, wherein said extracting step includes extracting internal information selected from the group consisting of $\mu_a$, $\mu_s'$, $\mu_{eff}$, $\eta$ and $z_0$.

7. A method of measuring a scattering medium according to claim 5, further comprising the following step:

calculating further internal information with respect to said specified absorptive constituents in said scattering medium by use of the internal information obtained in said extracting step.

8. A method of measuring a scattering medium according to claim 7, wherein said internal information obtained in said extracting step is the absorption coefficients, $\mu_a$, with respect to said wavelengths of said light and said calculating step includes calculating said further internal information that is selected from the group consisting of concentrations of the specified absorptive constituents and a ratio of the concentrations of the specified absorptive constituents.

9. A method of measuring a scattering medium according to claim 7, wherein said further internal information is selected from the group consisting of a concentration of reduced hemoglobin, (Hb), a concentration of oxyhemoglobin, (HbO), a concentration of hemoglobin, (Hb)+(HbO), and a degree of oxygen saturation of hemoglobin, Y.

10. A method of measuring a scattering medium according to claim 5, wherein said emitting step includes emitting light having a pulse shape, and said extracting step includes measuring light intensity as said measured values.

11. A method of measuring a scattering medium according to claim 5, wherein said detecting step includes measuring said at least three detected signals over a period of time and said extracting step includes integrating said at least three detected signals over said period of time to calculate said at least three measured values, $Q(\rho_i)$.

12. An apparatus for measuring a scattering medium comprising:

light-emitting means for emitting light having a single predetermined wavelength;

light-incident means for causing said light to be incident on the scattering medium at a light incidence position to allow said light to propagate through the scattering medium;

photodetecting means for detecting said light which has propagated through the scattering medium at at least three photodetection points, with distances, $\rho_i$, between the light incidence position and each of the photodetection points differing from one another, to obtain at least three detected signals; and arithmetic processing means for extracting internal information of the scattering medium with respect to said wavelength of said light, by converting said at least three detected signals to at least three measured values, $Q(\rho_i)$, and then performing arithmetic processing to said three or more measured values, $Q(\rho_i)$, based on a simultaneous relation of the following equation:

$$\ln Q(\rho_i) = \ln (\eta z_0/2\pi) - \frac{3}{2} \ln (z_0^2 + \rho_i^2) + \ln (\mu_{eff}(z_0^2 + \rho_i^2)^{1/2} + 1) - \mu_{eff}\sqrt{(z_0^2 + \rho_i^2)}$$

for $z_0 = a/(\mu_a + \mu_s')$ where i is an integer running from one to at least three, $\eta$ is a light attenuation factor, $\mu_{eff}$ is an effective attenuation coefficient $$\mu_{eff} = \sqrt{(3\mu_a(\mu_a + \mu_s'))} \quad,$$

a is a constant determined in accordance with a type of the scattering medium, $\mu_a$ is an absorption coefficient, and $\mu_s'$ is a transport scattering coefficient.

13. An apparatus for measuring a scattering medium according to claim 12, wherein said arithmetic processing means selects said internal information from the group consisting of $\mu_a$, $\mu_s'$, $\mu_{eff}$, $\eta$ and $z_0$.

14. An apparatus for measuring a scattering medium according to claim 12, wherein said light is light having a pulse shape, and said measured values are light intensities.

15. An apparatus for measuring a scattering medium according to claim 12, wherein said photodetecting means measures said three or more detected signals each said arithmetic processing means integrates for a period of time and integrate said three or more detected signals over said period of time to calculate said three or more measured values, $Q(\rho_i)$.

16. An apparatus for measuring a scattering medium comprising:

light-emitting means for emitting light having at least two predetermined wavelengths of which absorption coefficients to a specified absorptive constituent in said scattering medium differ from one another;

light-emitting means for causing said light to be incident on the scattering medium at a light incidence position to allow said light to propagate through the scattering medium;

photodetecting means for detecting said light which has been propagated through the scattering medium at at least three photodetection points, with distances, $\mu_i$, between the light incidence position and each of the photodetection points being different from each other, to obtain at least three detected signals with respect to each of said wavelengths of said light; and first arithmetic processing means for extracting internal information of the scattering medium with respect to each of said wavelengths of said light, by converting said at least three detected signals to at least three measured values, $Q(P_i)$, and then performing arithmetic processing to said at least three measured values, $Q(\rho_i)$, based on a simultaneous relation of the following equation:

$$\ln Q(\rho_i) = \ln (\eta z_0/2\pi) - \frac{3}{2} \ln (z_0^2 + \rho_i^2) + \ln (\mu_{\mathit{eff}}(z_0^2 + \rho_i^2)^{1/2} + 1) - \mu_{\mathit{eff}}\sqrt{(z_0^2 + \rho_i^2)}$$

for $z_0 = a/(\mu_a + \mu_s')$ where i is an integer running from one to at least three, $\eta$ represents a light attenuation factor, $\mu_{\mathit{eff}}$ is an effective attenuation coefficient $$\mu_{\mathit{eff}} = \sqrt{(3\mu_a(\mu_a + \mu'_s))} \quad ,$$

a is a constant determined in accordance with a type of the scattering medium, $\mu_a$ designates an absorption coefficient, and $\mu_s'$ is a transport scattering coefficient.

17. An apparatus for measuring a scattering medium according to claim 16, wherein said first arithmetic processing means selects said internal information from the group consisting of $\mu_a$, $\mu_s'$, $\mu_{\mathit{eff}}$, $\eta$ and $z_0$.

18. An apparatus for measuring a scattering medium according to claim 16, further comprising second arithmetic processing means for calculating further internal information with respect to said specified absorptive constituents in said scattering medium by use of the internal information obtained in said first arithmetic processing means.

19. An apparatus for measuring a scattering medium according to claim 18, wherein said internal information obtained in said first arithmetic processing means is absorption coefficients, $\mu_a$, with respect to said wavelengths of said light, and said further internal information obtained in said second arithmetic processing means is selected from the group consisting of concentrations of the specified absorptive constituents and a ratio of the concentrations of the specified absorptive constituents.

20. An apparatus for measuring a scattering medium according to claim 18, wherein said second arithmetic processing means selects said further internal information from the group consisting of a concentration of reduced hemoglobin, (Hb), a concentration of oxyhemoglobin, (HbO), a concentration of hemoglobin, (Hb)+(HbO), and a degree of oxygen saturation of hemoglobin.

21. An apparatus for measuring a scattering medium according to claim 16, wherein said light is light having a pulse shape, and said measured values are light intensities.

22. An apparatus for measuring a scattering medium according to claim 16, wherein said photodetecting means measures said three or more detected signals for a period of time and said arithmetic processing means integrates said three or more detected signals over said period of time to calculate said at least three measured values, $Q(\mu_i)$.

23. An apparatus for measuring a scattering medium according to claim 16, wherein said light-incident means is a light guide.

* * * * *